(12) United States Patent
Hori et al.

(10) Patent No.: US 10,029,216 B2
(45) Date of Patent: Jul. 24, 2018

(54) HOLLOW-FIBER MEMBRANE BLOOD PURIFICATION DEVICE

(71) Applicant: ASAHI KASEI MEDICAL CO., LTD., Tokyo (JP)

(72) Inventors: Ryoko Hori, Tokyo (JP); Yosuke Hata, Tokyo (JP); Junya Kawakami, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 61 days.

(21) Appl. No.: 15/104,072

(22) PCT Filed: Dec. 16, 2014

(86) PCT No.: PCT/JP2014/083309
§ 371 (c)(1),
(2) Date: Jun. 13, 2016

(87) PCT Pub. No.: WO2015/093493
PCT Pub. Date: Jun. 25, 2015

(65) Prior Publication Data
US 2016/0354728 A1 Dec. 8, 2016

(30) Foreign Application Priority Data

Dec. 16, 2013 (JP) .................................. 2013-259551

(51) Int. Cl.
*B01D 69/14* (2006.01)
*A61M 1/16* (2006.01)
(Continued)

(52) U.S. Cl.
CPC ......... *B01D 69/144* (2013.01); *A61M 1/1621* (2014.02); *B01D 63/02* (2013.01);
(Continued)

(58) Field of Classification Search
CPC ... A61M 1/16; A61M 1/1621; B01D 2323/08; B01D 2323/12; B01D 2323/22;
(Continued)

(56) References Cited

U.S. PATENT DOCUMENTS

2009/0139925 A1 6/2009 Sternberg
2010/0133170 A1 6/2010 Satoh et al.

FOREIGN PATENT DOCUMENTS

EP 0 923 955 6/1999
JP 7-178166 7/1995
(Continued)

OTHER PUBLICATIONS

Search Report issued in Japan Patent Application No. PCT/JP2014/083309, dated Jan. 20, 2015.
(Continued)

*Primary Examiner* — John Kim
(74) *Attorney, Agent, or Firm* — Greenblum & Bernstein, P.L.C.

(57) ABSTRACT

Disclosed is a hollow-fiber membrane blood purification device having an improved antioxidant performance, good water permeation performance and blood compatibility performance, and economic rationality. The present invention provides a hollow-fiber membrane blood purification device including hollow-fiber membranes filled in a vessel, in which the hollow-fiber membranes contain a hydrophobic polymer, a hydrophilic polymer and a fat-soluble vitamin, when a hollow-fiber membrane bundle is divided into five sections in a lengthwise direction and divided sections positioned in endmost portions are defined as body end portions, an amount of the fat-soluble vitamin present in at least one of the body end portions is the largest among amounts of the fat-soluble vitamin present respectively in all the divided sections, and an amount of the fat-soluble
(Continued)

vitamin per m² of a hollow-fiber membrane inner surface of the at least one body end portion is 20 mg/m² or more and 300 mg/m² or less.

17 Claims, 2 Drawing Sheets

(51) Int. Cl.
    *B01D 69/08*     (2006.01)
    *B01D 63/02*     (2006.01)
    *C08L 33/12*     (2006.01)
    *C08L 81/06*     (2006.01)
    *B01D 67/00*     (2006.01)
    *B01D 65/10*     (2006.01)
    *B01D 71/68*     (2006.01)

(52) U.S. Cl.
CPC ........... *B01D 63/021* (2013.01); *B01D 65/10* (2013.01); *B01D 67/0088* (2013.01); *B01D 69/08* (2013.01); *B01D 71/68* (2013.01); *C08L 33/12* (2013.01); *C08L 81/06* (2013.01); *A61M 1/16* (2013.01); *B01D 63/023* (2013.01); *B01D 2323/08* (2013.01); *B01D 2323/12* (2013.01); *B01D 2323/22* (2013.01); *B01D 2325/06* (2013.01); *C08L 2201/08* (2013.01); *C08L 2203/02* (2013.01); *C08L 2203/12* (2013.01); *C08L 2205/025* (2013.01)

(58) Field of Classification Search
CPC .. B01D 2325/06; B01D 63/02; B01D 63/021; B01D 63/023; B01D 65/10; B01D 67/0088; B01D 69/08; B01D 69/144; B01D 71/68; C08L 2201/08; C08L 2203/02; C08L 2203/12; C08L 2205/025; C08L 33/12; C08L 81/06
See application file for complete search history.

(56) References Cited

FOREIGN PATENT DOCUMENTS

| JP | 11-347117 | 12/1999 |
|----|-----------|---------|
| JP | 2006-296931 | 11/2006 |
| JP | 2013-9761 | 1/2013 |
| JP | 2013-094525 | 5/2013 |
| JP | 5351394 | 11/2013 |

OTHER PUBLICATIONS

International Preliminary Report on Patentability/Written Opinion and English language translation thereof, dated Jan. 20, 2015.
Search Report issued in European Patent Office (EPO) Patent Application No. 14872034.5, dated Nov. 7, 2016.

HOLLOW-FIBER MEMBRANE BLOOD PURIFICATION DEVICE

TECHNICAL FIELD

The present invention relates to a hollow-fiber membrane blood purification device.

BACKGROUND ART

In a conventional blood purification therapy employed for treating renal failure and the like, hollow-membrane blood purification devices such as a hemodialyzer, a hemofilter and a hemodiafilter including, as a separation material, a hollow-fiber membrane using a polymer such as cellulose, cellulose acetate, polysulfone, polyethersulfone, polymethyl methacrylate or polyacrylonitrile have been widely used for purpose of removing uremic toxins and body wastes from blood.

As these hollow-fiber membrane blood purification devices, a polysulfone-based hollow-fiber membrane and a polyethersulfone-based hollow-fiber membrane are widely used because such membranes are excellent in reduction of the amount of blood to be extracorporeally circulated, high efficiency of removing uremic toxic substances from blood, and high productivity in module production, and are particularly capable of simultaneously attaining both high permeability and blood compatibility (Patent Documents 1 and 2).

In recent years, not only for purpose of removing uremic toxins and body wastes from blood but also for relieving oxidative stress apparently occurring in a patient on dialysis for a long period of time, attempts are made, for example, to use a separation membrane for eliminating a peroxide, that is, a causative substance of the oxidative stress, or to restore an antioxidant effect of a living body.

Patent Documents 3 and 4 propose a hollow-fiber membrane blood purification device in which a fat-soluble vitamin, such as vitamin E, having various physiological actions including an in vivo antioxidant effect, a biological membrane stabilizing action, and a platelet aggregation inhibiting action is introduced into a hollow-fiber membrane. It is known that a polysulfone-based hollow-fiber membrane and a polyethersulfone-based hollow-fiber membrane have high affinity with a fat-soluble vitamin capable of effectively inhibiting the oxidative stress caused through extracorporeal blood circulation, and hence the fat-soluble vitamin can be easily immobilized on the hollow-fiber membrane.

Meanwhile, cases of complications occurring in the blood purification therapy, such as disequilibrium syndrome presenting a symptom of headache, nausea or vomiting derived from an osmotic difference caused between blood in which a uremic toxin concentration has been abruptly lowered and a body tissue in which the uremic toxin concentration is easily retained, have been continuously reported even today, and these complications do not immediately induce risk of death or serious physical impediment but are painful to the patient.

CITATION LIST

Patent Document

Patent Document 1: Japanese Patent Laid-Open No. 7-178166
Patent Document 2: Japanese Patent Laid-Open No. 2006-296931
Patent Document 3: Japanese Patent Laid-Open No. 2013-9761
Patent Document 4: Japanese Patent Laid-Open No. 2013-94525

SUMMARY OF INVENTION

Technical Problem

It is regarded that complications can be relieved by using a hollow-fiber membrane blood purification device in which the fat-soluble vitamin is introduced into a hollow-fiber membrane, but in order to further reduce the burden of a patient, a hollow-fiber membrane blood purification device having a more efficient antioxidant performance is desired.

In earnest studies made in consideration of the aforementioned circumstances, increase of the amount of the fat-soluble vitamin to be immobilized for further improving the antioxidant performance has been examined, resulting in finding that the amount of the fat-soluble vitamin to be immobilized cannot be simply increased due to a problem described later.

As a method for introducing a fat-soluble vitamin into a hollow-fiber membrane, roughly two methods have been proposed. One is a method in which a fat-soluble vitamin is added to a spinning dope (for example, Patent Document 4), and the other is a method in which a hollow-fiber membrane is coated with a fat-soluble vitamin (for example, Patent Document 3).

In a hollow-fiber membrane blood purification device produced by any of these methods, the fat-soluble vitamin is distributed substantially uniformly in the lengthwise direction of the hollow-fiber membrane blood purification device. It was found, in this device, that if the amount of the fat-soluble vitamin to be immobilized on the whole hollow-fiber membranes of the hollow-fiber membrane blood purification device is increased for improving the antioxidant performance, there arise disadvantages that the water permeability of the whole hollow-fiber membranes is degraded, that the blood compatibility is lowered, and that the resultant device is not economical.

Accordingly, the present inventors focused on the following:

In actual blood circulation performed in the blood purification therapy, it is a blood inlet port portion of a hollow-fiber membrane blood purification device that the concentration of a peroxide substance present in blood passing through the hollow-fiber membrane blood purification device is the highest. In other words, a fat-soluble vitamin is consumed in a largest amount in the blood inlet port portion in the hollow-fiber membrane blood purification device.

Besides, when blood passes through the hollow-fiber membrane blood purification device, reactive oxygen is produced through interaction between the hollow-fiber membrane and the blood, and therefore, the fat-soluble vitamin is probably consumed in a large amount also in a blood outlet port portion of the hollow-fiber membrane blood purification device. As a result, the fat-soluble vitamin is relatively largely consumed in both end portions of the hollow-fiber membrane blood purification device, and hence, it is presumed that if the amount of the fat-soluble vitamin to be immobilized in these portions alone is increased, the antioxidant performance higher than in the conventional technique can be attained without causing the water permeability degradation, the lowering of the blood compatibility and cost increase.

Besides, when a center portion and an outside portion of a hollow-fiber membrane bundle are compared with each other, it was found that the amount of blood passing through the center portion is larger than that passing through the outside portion. The center portion and the outside portion of the hollow-fiber membrane bundle will be described later.

In the actual blood circulation performed in the blood purification therapy, the center portion of the hollow-fiber membrane blood purification device is affected by a linear velocity and hence the amount of blood passing therethrough is increased, and therefore, in the hollow-fiber membrane blood purification device, the concentration of a peroxide substance present in the blood is relatively higher in the center portion than in the outside portion. In other words, the fat-soluble vitamin is relatively largely consumed in the center portion of the hollow-fiber membrane blood purification device.

In the background art, there was no hollow-fiber membrane blood purification device devised in consideration of the aforementioned points.

Accordingly, an object of the present invention is to provide a hollow-fiber membrane blood purification device having an improved antioxidant performance, good water permeation performance and blood compatibility performance, and economic rationality.

Solution to Problem

As a result of making earnest studies for solving the aforementioned problem, the present inventors have found that the problem to be solved by the present invention can be overcome by controlling the amount of a fat-soluble vitamin present in a hollow-fiber membrane bundle in a hollow-fiber membrane blood purification device in which hollow-fiber membranes are filled in a vessel, and thus, the present invention has been accomplished.

Specifically, the present invention provides the following:
(1) A hollow-fiber membrane blood purification device comprising hollow-fiber membranes filled in a vessel,
wherein the hollow-fiber membranes contain a hydrophobic polymer, a hydrophilic polymer and a fat-soluble vitamin,
when a hollow-fiber membrane bundle is divided into five sections in a lengthwise direction and divided sections positioned in endmost portions are defined as body end portions, an amount of the fat-soluble vitamin present in at least one of the body end portions is largest among amounts of the fat-soluble vitamin present respectively in all the divided sections, and an amount of the fat-soluble vitamin per $m^2$ of a hollow-fiber membrane inner surface of the at least one body end portion is 20 $mg/m^2$ or more and 300 $mg/m^2$ or less.
(2) The hollow-fiber membrane blood purification device according to (1), wherein when an amount of the fat-soluble vitamin per $m^2$ of the hollow-fiber membrane inner surface present in the body end portion where the amount of the fat-soluble vitamin is the largest is defined as A ($mg/m^2$) and an amount of the fat-soluble vitamin per $m^2$ of the hollow-fiber membrane inner surface present in a divided section where the amount of the fat-soluble vitamin is the smallest among the other divided sections is defined as B (mg/m2), a ratio (A/B) between the amounts A and B is 1.1 or more and 10 or less.
(3) The hollow-fiber membrane blood purification device according to (2), wherein the ratio (A/B) between the amounts A and B is 1.3 or more and 10 or less.

(4) The hollow-fiber membrane blood purification device according to any one of (1) to (3), wherein when within an inner circle having a ½ radius of the hollow-fiber membrane bundle is defined as a center portion and a portion not included in the center portion is defined as an outside portion, an amount of the fat-soluble vitamin per $m^2$ of the hollow-fiber membrane inner surface present in the center portion is larger than an amount of the fat-soluble vitamin per $m^2$ of the hollow-fiber membrane inner surface present in the outside portion.
(5) The hollow-fiber membrane blood purification device according to (4), wherein when the amount of the fat-soluble vitamin per $m^2$ of the hollow-fiber membrane inner surface present in the center portion is defined as C ($mg/m^2$) and the amount of the fat-soluble vitamin per $m^2$ of the hollow-fiber membrane inner surface present in the outside portion is defined as D ($mg/m^2$), a ratio (C/D) between the amounts C and D is 1.1 or more and 50 or less.
(6) The hollow-fiber membrane blood purification device according to any one of (1) to (5), wherein the hydrophobic polymer has a solubility parameter S $(cal/cm^3)^{1/2}$ of 13.0 or less.
(7) The hollow-fiber membrane blood purification device according to any one of (1) to (6), wherein the hydrophobic polymer is any one selected from the group consisting of polysulfones, polyethersulfones and cellulose acetates.
(8) The hollow-fiber membrane blood purification device according to any one of (1) to (7), wherein the hydrophilic polymer is polyvinylpyrrolidone.

Advantageous Effects of Invention

According to the present invention, a hollow-fiber membrane blood purification device having an improved antioxidant performance, good water permeation performance and blood compatibility performance, and economic rationality can be provided.

DESCRIPTION OF EMBODIMENTS

Figure 1:
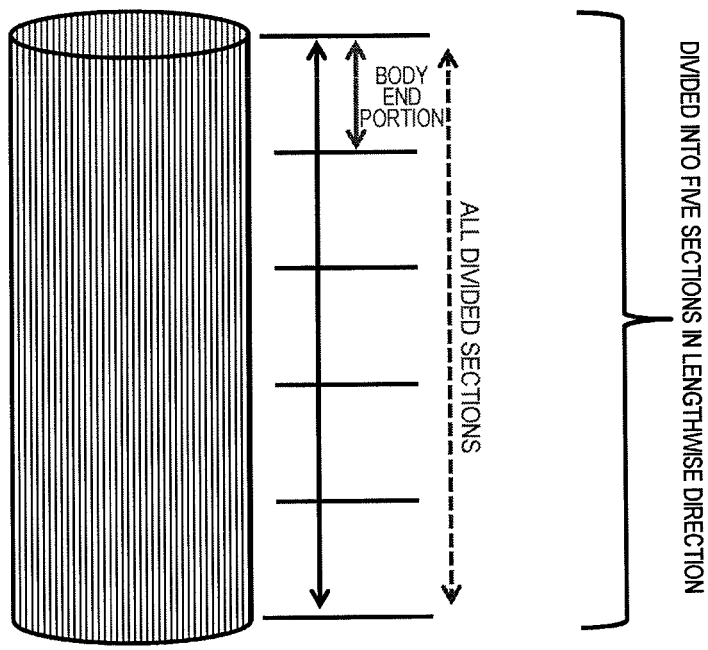
FIG. 1 illustrates a case in which a hollow-fiber membrane blood purification device has one body end portion where the amount of a fat-soluble vitamin is the largest.

Now, an embodiment for practicing the present invention (hereinafter, referred to as the "present embodiment") will be described in detail. It is noted that the present invention is not limited to the following embodiment but can be variously modified within the scope thereof.

A hollow-fiber membrane blood purification device of the present embodiment is a hollow-fiber membrane blood purification device in which hollow-fiber membranes are filled in a vessel; the hollow-fiber membranes contain a hydrophobic polymer, a hydrophilic polymer and a fat-soluble vitamin; when a hollow-fiber membrane bundle is divided into five sections in a lengthwise direction and divided sections positioned in endmost portions are defined as body end portions, an amount of the fat-soluble vitamin present in at least one of the body end portions is the largest among the amounts of the fat-soluble vitamin present respectively in all the divided sections, and the amount of the fat-soluble vitamin per $m^2$ of a hollow-fiber membrane inner surface of the at least one body end portion is 20 $mg/m^2$ or more and 300 $mg/m^2$ or less.

The "hollow-fiber membrane blood purification device" of the present invention refers to equipment for purifying blood to be used in a blood extracorporeal circulation therapy such as a hemodialyzer, a hemodialysis filter, a hemofilter or a continuous hemo(dia) filter.

<Hollow-Fiber Membrane>

In the present embodiment, a "hollow-fiber membrane" refers to a membrane in the shape of a hollow fiber for a blood treatment used in a hollow-fiber membrane blood purification device.

The form of the hollow-fiber membrane such as the inner diameter, the thickness and the length can be arbitrarily controlled, and for example, the inner diameter can be 100 μm or more and 300 μm or less, the thickness can be 10 μm or more and 100 μm or less, and the length can be 10 μm or more and 40 cm or less.

It may be what is called an asymmetric membrane including a thin dense layer (activity separation layer) for simultaneously attaining both a high molecular-weight fractionation property and high water permeability, and a porous layer (support layer) bearing the strength of the hollow-fiber membrane, or a symmetric membrane including merely a thin dense layer (activity separation layer) with molecular weight fractionation regarded significant.

In the present embodiment, the "hollow-fiber membrane inner surface" refers to a surface on the side of a hollow portion of the hollow-fiber membrane.

In the hollow-fiber membrane blood purification device of the present embodiment, the hollow-fiber membrane is filled in a vessel constituting the hollow-fiber membrane blood purification device, and a plurality of hollow-fiber membranes are filled in the form of a bundle of the hollow-fiber membranes.

<Hydrophobic Polymer>

In the present embodiment, the hydrophobic polymer refers to a synthetic polymer or a natural polymer that is not dissolved in water or does not have affinity with water.

The hydrophobic polymer is not especially limited, and examples thereof include polysulfone-based resins such as polysulfone, polyethersulfone, and a polymer alloy of polyethersulfone-polyarylate; methacrylate-based resins such as polymethyl methacrylate, polyhydroxyethyl methacrylate, and copolymers containing methyl methacrylate or hydroxyethyl methacrylate; polyolefins such as polyethylene, polypropylene, poly-3-methylbutene-1, and poly-4-methylpentene-1; cellulose acetates such as cellulose triacetate and cellulose diacetate; and polyacrylonitrile, polyamide, polyarylate, polycarbonate, polyether ether ketone, and polyallyl ether ketone.

As the hydrophobic polymer, these may be used singly or in combinations of two or more.

Among these, the synthetic polymers are preferred from the viewpoint of homogeneity in the composition as a polymer, and polysulfone, a polymer alloy of polyethersulfone-polyarylate, polymethyl methacrylate and polyethylene are more preferred because these polymers have been suitably used for blood purification in a large number of clinical cases and are excellent in stable supply as a raw material.

The polysulfone-based resins include polyphenylsulfone, polyallyl ether sulfone and the like, and may be a compound in which a part of an aromatic ring is chemically modified.

The polysulfone-based resins are not especially limited, and examples thereof include polymers having a repeating unit represented by any of the following formulas (1) to (5). In this formula, n represents a degree of polymerization and may be an arbitrary value.

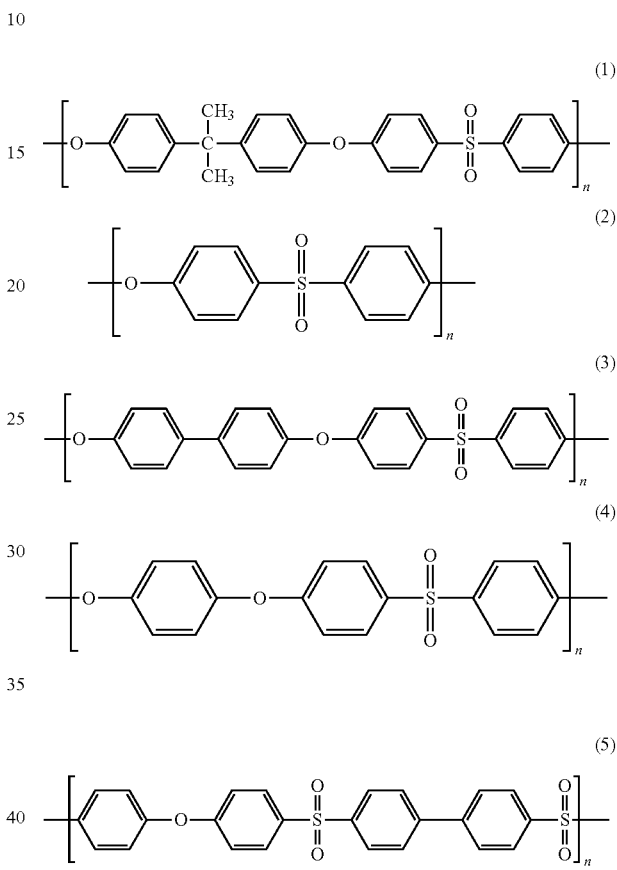

A polysulfone of formula (1) is not especially limited, and examples thereof include a product available under a product name of "Udel" from Solvay Advanced Polymers (hereinafter designated as "Solvay"), and a product available under a product name of "Ultrazone" from BASF Japan Ltd., and there are a plurality of types in accordance with the degree of polymerization.

A polyethersulfone of formula (2) is not especially limited, and examples thereof include a product available under a trade name of "Sumika Excel PES" from Sumitomo Chemical Co., Ltd, and a product available under a trade name of "Ultrazone" from BASF Japan Ltd. From the viewpoint of handleability and easy availability, a reduced viscosity measured by using a 1 (W/V) % dimethylformamide solution is preferably 0.30 to 0.60, and more preferably 0.36 to 0.50.

A polyarylate is not especially limited, and an example includes a polymer having a repeating unit represented by the following formula (6), and a compound in which a part of an aromatic ring is chemically modified may be used. In this formula, n represents a degree of polymerization and may be an arbitrary value.

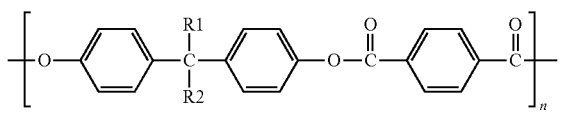

(6)

In formula (6), R1 and R2 represent a lower alkyl group having 1 to 5 carbon atoms. R1 and R2 may be the same as or different from each other.

Examples of R1 and R2 include a methyl group, an ethyl group, a propyl group, a butyl group and a pentyl group.

From the viewpoint of the handleability and the easy availability, the polyarylate preferably has a molecular weight of about 20,000 to 50,000.

As the polyarylate, a polyarylate appropriately synthesized by polycondensation of a bivalent phenol and an aromatic dicarboxylic acid may be used, or a commercially available product may be used.

The commercially available product is not especially limited, and examples thereof include products available under a product name of "U polymer" from Unitika Ltd., a product name of "APE" from Bayer, a product name of "DUREL" from Celanese Corporation, and a product name of "Arylon" from Du Pont.

The methacrylate-based resins are not especially limited, and an example includes a polymethyl methacrylate having a repeating unit represented by the following formula (7). In this formula, n represents a degree of polymerization and may be an arbitrary value.

The polymethyl methacrylate is not especially limited, and an example includes a product available under a product name of "Dianal BR-80" from Mitsubishi Rayon Co., Ltd.

(7)

The polyolefins are not especially limited, and examples thereof include polyethylene, polypropylene, poly-3-methylbutene-1, and poly-4-methylpentene-1.

Among these, polyethylene and polypropylene are preferred because a hollow-fiber membrane having a sufficiently large pore size can be obtained by using these.

The polyethylene is not especially limited but has a repeating unit represented by the following formula (8), and examples thereof include products available under a product name of "HI-ZEX 2208J" from Prime Polymer Co., Ltd. and a product name of "Suntec HdJ240" from Asahi Kasei Chemicals Corp.

(8)

<Hydrophilic Polymer>

In the present embodiment, the hydrophilic polymer is not especially limited, and examples thereof include polyvinylpyrrolidone, polyethylene glycol, polyvinyl alcohol, polypropylene glycol, and an ethylene-vinyl alcohol copolymer.

From the viewpoint of spinning stability and affinity with a polysulfone-based resin, polyvinylpyrrolidone is preferably used.

As the hydrophilic polymer, these may be used singly or in combinations of two or more.

The polyvinylpyrrolidone is not especially limited, and an example includes a product available under a product name of "Plasdone" from BASF Japan Ltd., and there are products having different molecular weights such as K-15, -30 and -90.

The ethylene-vinyl alcohol copolymer is not especially limited, and examples thereof include products available under a product name of "Soarnol E" from Nippon Synthetic Chemical Industry Co., Ltd., and a product name of "Eval" from Kuraray Co., Ltd.

<Fat-Soluble Vitamin>

In the present embodiment, the fat-soluble vitamin is not especially limited, and examples thereof include vitamin A, vitamin D, vitamin E and vitamin K.

Among these, vitamin E is preferred from the viewpoint that it does not induce a damage even when overdosed.

As the fat-soluble vitamin, these may be used singly or in combinations of two or more.

The vitamin E is not especially limited, and examples thereof include α-tocopherol, α-tocopherol acetate, α-tocopherol nicotinate, β-tocopherol, γ-tocopherol, and δ-tocopherol.

Among these, α-tocopherol is preferred because it is excellent in various physiological actions including an in vivo antioxidant effect, a biological membrane stabilizing action and a platelet aggregation inhibiting action, and has a high effect of suppressing oxidative stress.

<Fat-Soluble Vitamin Present in Each Divided Section Obtained by Dividing Hollow-Fiber Membrane Bundle into Five Sections in Lengthwise Direction>

Figure 2:
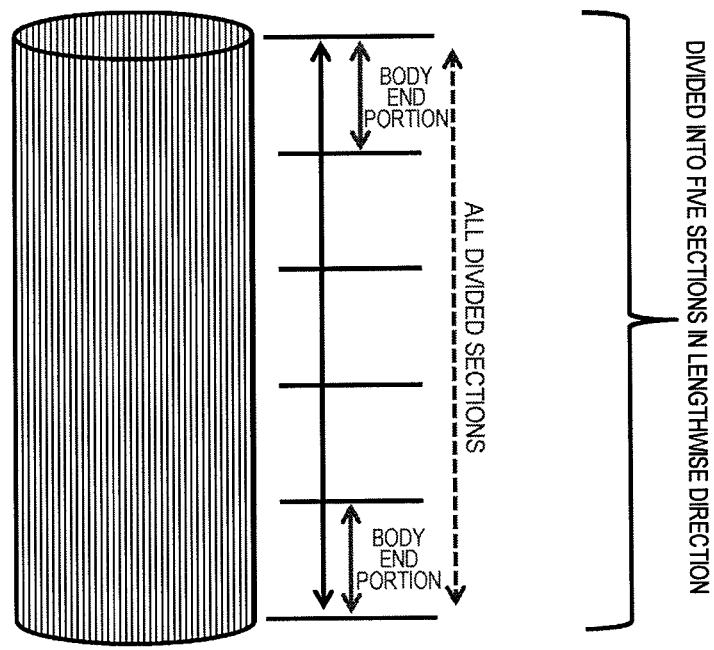
FIG. 2 illustrates a case in which a hollow-fiber membrane blood purification device has two body end portions where the amount of a fat-soluble vitamin is the largest.

In the present embodiment, a section positioned in an endmost portion when the hollow-fiber membrane bundle is divided into five sections in the lengthwise direction is defined as a body end portion (FIGS. 1 and 2).

As illustrated in FIG. 2, one hollow-fiber membrane blood purification device has two body end portions.

In blood circulation, one of these body end portions corresponds to a blood inlet side and the other corresponds to a blood outlet side.

Figure 3:
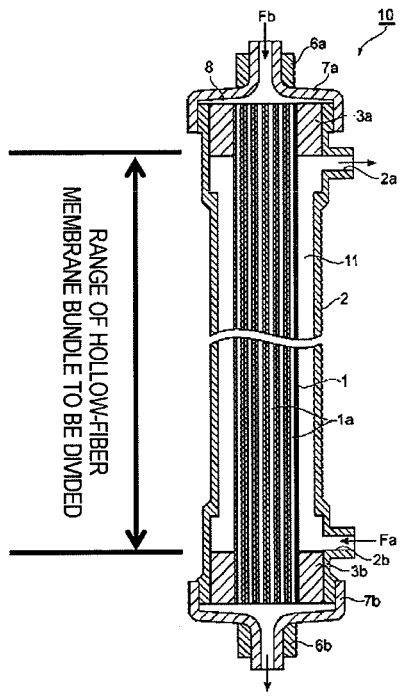
FIG. 3 illustrates a typical hollow-fiber membrane blood purification device, and also illustrates an example of a range of a hollow-fiber membrane bundle in the hollow-fiber membrane blood purification device.

In the present embodiment, the hollow-fiber membrane bundle refers to a portion substantially having the ability of a blood treatment in the hollow-fiber membrane blood purification device, and corresponds, for example, to a portion present between potting layers (each corresponding to a boundary between a potting agent-added region and a non-potting agent-added region) disposed at both ends of the hollow-fiber membrane blood purification device when the hollow-fiber membrane blood purification device is disassembled (FIG. 3).

<Fat-Soluble Vitamin Present in Center Portion and Outside Portion with Center Portion Defined as within Inner Circle Having ½ Radius of Hollow-Fiber Membrane Bundle and Outside Portion Defined as Portion not Included in Center Portion>

In the present embodiment, a circle having a ½ radius in a cross-sectional direction of the hollow-fiber membrane bundle is defined as an inner circle. In addition, a portion within the inner circle in the cross-sectional direction of the hollow-fiber membrane bundle is defined as a center portion, and a portion not included in the center portion is defined as an outside portion (FIG. 4).

Figure 4:
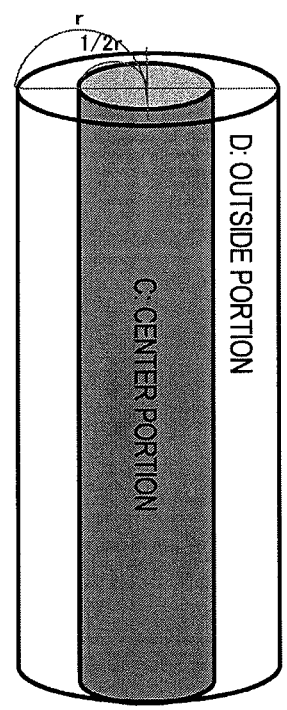
FIG. 4 is a diagram schematically illustrating a center portion and an outside portion of the hollow-fiber membrane bundle.

In other words, when a portion corresponding to the outer circumference of the hollow-fiber membrane bundle is defined as an outer circle and a circle having a ½ radius in the cross-sectional direction is defined as an inner circle, a portion of the hollow-fiber membrane bundle not included in the inner circle, namely, a portion having a radius of the ½ radius or more within the outer circumference (corresponding to the radius) in the cross-sectional direction, is defined as the outside portion (FIG. 4).

<Distribution of Fat-Soluble Vitamin>

In the present embodiment, the amount of the fat-soluble vitamin present at least one of the body end portions is the largest among the amounts of the fat-soluble vitamin present respectively in all the divided sections. Besides, the amount of the fat-soluble vitamin present in the center portion is preferably larger than the amount of the fat-soluble vitamin present in the outside portion.

As described in examples below, if the amount of the fat-soluble vitamin per $m^2$ of the hollow-fiber membrane inner surface in the body end portion or the center portion is compared with the amount of the fat-soluble vitamin per $m^2$ of the hollow-fiber membrane inner surface in the other divided sections or the outside portion, it can be determined that the amount of the fat-soluble vitamin present in the body end portion or the center portion is larger than the amounts of the fat-soluble vitamin present respectively in the other divided sections or the outside portion. Incidentally, a hollow-fiber membrane present on the circumference of the inner circle of the hollow-fiber membrane bundle is regarded to belong to the center portion.

In actual blood circulation, it is in blood outlet/inlet port portions of the hollow-fiber membrane blood purification device that the concentration of a peroxide substance present in blood passing through the hollow-fiber membrane blood purification device is the highest. If the amount of the fat-soluble vitamin present in the body end portion on the blood inlet side of the hollow-fiber membrane blood purification device is the largest, the peroxide substance is efficiently eliminated by the fat-soluble vitamin. Besides, if the amount of the fat-soluble vitamin present in the body end portion on the blood outlet side of the hollow-fiber membrane blood purification device is the largest, reactive oxygen produced through the interaction between the hollow-fiber membrane and the blood is efficiently eliminated. The amounts of the fat-soluble vitamin in the two body end portions may be set to be the largest, so that both the peroxide substance and the reactive oxygen can be efficiently eliminated.

Besides, when compared between the center portion and the outside portion of the hollow-fiber membrane blood purification device, the concentration of the peroxide substance present in the blood passing through the hollow-fiber membrane blood purification device is higher in the center portion where the amount of blood is increased due to the influence of a linear velocity than in the outside portion. Therefore, if the amount of the fat-soluble vitamin is larger in the center portion than in the outside portion, the peroxide substance is efficiently eliminated by the fat-soluble vitamin. Besides, the reactive oxygen produced through the interaction between the hollow-fiber membrane and the blood can be efficiently eliminated.

In the present embodiment, a value, in terms of an area of the hollow-fiber membrane inner surface, of the amount of the fat-soluble vitamin present in at least one of the body end portions, namely, the amount of the fat-soluble vitamin per $m^2$ of the hollow-fiber membrane inner surface of the body end portion, is 20 mg/$m^2$ or more and 300 mg/$m^2$ or less, preferably 20 mg/$m^2$ or more and 250 mg/$m^2$ or less, and more preferably 20 mg/$m^2$ or more and 200 mg/$m^2$ or less. If the amount of the fat-soluble vitamin is 20 mg/$m^2$ or more, the effect resulting from the use of the fat-soluble vitamin can be attained, and if the amount is 300 mg/$m^2$ or less, excellent blood compatibility performance and water permeation performance can be attained.

In the present embodiment, a value, in terms of the area of the hollow-fiber membrane inner surface, of the amount of the fat-soluble vitamin present in the center portion, namely, the amount of the fat-soluble vitamin per $m^2$ of the hollow-fiber membrane inner surface of the center portion, is preferably 20 mg/$m^2$ or more and 300 mg/$m^2$ or less, more preferably 20 mg/$m^2$ or more and 250 mg/$m^2$ or less, and further preferably 20 mg/$m^2$ or more and 200 mg/$m^2$ or less. If the amount of the fat-soluble vitamin is 20 mg/$m^2$ or more, the effect resulting from the use of the fat-soluble vitamin can be attained, and if the amount is 300 mg/$m^2$ or less, excellent blood compatibility performance and water permeation performance can be attained.

In the present embodiment, it is preferable that the amount of the fat-soluble vitamin per $m^2$ of the hollow-fiber membrane inner surface present in at least one of the body end portions is the largest among the amounts of the fat-soluble vitamin present respectively in all the divided sections; that the amount of the fat-soluble vitamin per $m^2$ of the hollow-fiber membrane inner surface present in the at least one body end portion is 20 mg/$m^2$ or more and 300 mg/$m^2$ or less; and that, when the portion within the inner circle having a ½ radius of the hollow-fiber membrane bundle is defined as the center portion and the portion not included in the center portion is defined as the outside portion, the amount of the fat-soluble vitamin per $m^2$ of the hollow-fiber membrane inner surface present in the center portion is larger than the amount of the fat-soluble vitamin per $m^2$ of the hollow-fiber membrane inner surface present in the outside portion.

The amount of the fat-soluble vitamin per $m^2$ of the hollow-fiber membrane inner surface present in the center portion is preferably 20 mg/$m^2$ or more and 300 mg/$m^2$ or less, more preferably 20 mg/$m^2$ or more and 250 mg/$m^2$ or less, and further preferably 20 mg/$m^2$ or more and 200 mg/$m^2$ of less. Besides, when the amounts of the fat-soluble vitamin present in the center portion and the outside portion are respectively within the preferable ranges, the amount of the fat-soluble vitamin per $m^2$ of the hollow-fiber membrane inner surface present in at least one body end portion is preferably 20 mg/$m^2$ or more and 250 mg/$m^2$ or less, and more preferably 20 mg/$m^2$ or more and 200 mg/$m^2$ or less.

In the present invention, the term "amount of the fat-soluble vitamin present in a hollow-fiber membrane" means a content of the fat-soluble vitamin adhering to, adsorbed by or coated on the hollow-fiber membrane, and the amount of the fat-soluble vitamin present in the hollow-fiber membrane can be quantitatively determined, for example, depending on the content of the fat-soluble vitamin extracted by using a solvent without breaking or dissolving the hollow-fiber membrane.

An example of a method for measuring the amount of the fat-soluble vitamin present in the hollow-fiber membrane will now be described.

A hollow-fiber membrane blood purification device is disassembled, and a hollow-fiber membrane thus taken out is washed with water and dried. To the hollow-fiber membrane having been dried and precisely weighed, a surfactant capable of dissolving a fat-soluble vitamin, such as 1% by mass polyethylene glycol-t-octylphenylether aqueous solution, is added, followed by stirring and extracting. A hollow-fiber membrane inner surface area of the extracted hollow-fiber membrane is calculated on the basis of the inner diameter and the length of the hollow-fiber membrane.

In measuring the amounts of the fat-soluble vitamin present respectively in a center portion and an outside portion of hollow-fiber membranes, a hollow-fiber membrane blood purification device is disassembled, divided into the center portion and the outside portion, and the hollow-fiber membranes are collected from the respective portions for the measurement.

The quantitative measurement operation is performed, for example, by liquid chromatography, so as to calculate the concentration of the fat-soluble vitamin in an extract by using a calibration curve obtained based on a peak area of a fat-soluble vitamin standard solution.

The liquid chromatography, which is merely exemplarily described, can be performed as follows: A column (ODP-506E packed column for HPLC manufactured by Shodex Asahipak) is attached to a high-performance liquid chromatograph (pump: Jasco Corporation PU-1580, detector: Shimadzu RID-6A, auto-injector: Shimadzu SIL-6B, data processor: Tosoh GPC-8020, column oven: GL Sciences 556), methanol for high-performance liquid chromatography used as a mobile phase is allowed to pass therethrough at a column temperature of 40° C. and a flow rate of, for example, 1 mL/min, and the concentration of the fat-soluble vitamin is obtained on the basis of an area of an absorption peak at a wavelength of 295 nm detected by a UV detector.

In the present embodiment, when the amount of the fat-soluble vitamin per $m^2$ of the hollow-fiber membrane inner surface present in the at least one body end portion where the amount of the fat-soluble vitamin is the largest is defined as A ($mg/m^2$) and the amount of the fat-soluble vitamin per $m^2$ of the hollow-fiber membrane inner surface present in a divided section where the amount of the fat-soluble vitamin is the smallest among the other divided sections is defined as B ($mg/m^2$), a ratio (A/B) between the amounts A and B is preferably 1.1 or more and 10 or less, more preferably 1.3 or more and 10 or less, and further preferably 1.3 or more and 5.0 or less.

If the ratio A/B is 1.1 or more, the hollow-fiber membrane blood purification device is excellent in the antioxidant performance, and if the ratio A/B is 10 or less, the amount of the fat-soluble vitamin immobilized in the divided sections other than the body end portions of the hollow-fiber membrane blood purification device can be appropriate, and hence the hollow-fiber membrane blood purification device is excellent in the antioxidant performance as a whole.

When the amount of the fat-soluble vitamin per $m^2$ of the hollow-fiber membrane inner surface present in the center portion is defined as C ($mg/m^2$) and the amount of the fat-soluble vitamin per $m^2$ of the hollow-fiber membrane inner surface present in the outside portion is defined as D ($mg/m^2$), a ratio (C/D) between the amounts C and D is preferably 1.1 or more and 50 or less, more preferably 1.3 or more and 50 or less, still more preferably 2.0 or more and 50 or less, and further preferably 4.0 or more and 50 or less.

If the ratio C/D is 1.1 or more, the hollow-fiber membrane blood purification device is excellent in the antioxidant performance, and if the ratio C/D is 50 or less, the amount of the fat-soluble vitamin immobilized in the outside portion of the hollow-fiber membrane blood purification device can be appropriate, and hence the hollow-fiber membrane blood purification device is excellent in the antioxidant performance as a whole.

In the present embodiment, since variation in the antioxidant performance can be thus suppressed, it is preferable that the amount of the fat-soluble vitamin present in at least one body end portion is the largest among the amounts of the fat-soluble vitamin present respectively in all the divided sections, and that the amount of the fat-soluble vitamin per $m^2$ of the hollow-fiber membrane inner surface present in the center portion is larger than the amount of the fat-soluble vitamin per $m^2$ of the hollow-fiber membrane inner surface present in the outside portion.

In addition, when the amount of the fat-soluble vitamin per $m^2$ of the hollow-fiber membrane inner surface present in the center portion is defined as C ($mg/m^2$) and the amount of the fat-soluble vitamin per $m^2$ of the hollow-fiber membrane inner surface present in the outside portion is defined as D ($mg/m^2$), the ratio (C/D) is preferably 1.1 or more and 50 or less, and when the amount of the fat-soluble vitamin per $m^2$ of the hollow-fiber membrane inner surface present in the body end portion where the amount of the fat-soluble vitamin is the largest is defined as A ($mg/m^2$) and the amount of the fat-soluble vitamin per $m^2$ of the hollow-fiber membrane inner surface present in the divided section where the amount of the fat-soluble vitamin is the smallest among the other divided sections is defined as B ($mg/m^2$), the ratio (A/B) between the amounts A and B is preferably 1.1 or more and 10 or less.

In the present embodiment, it is suitable that the ratio A/B is 1.1 or more and 10 or less and that the ratio C/D is 1.1 or more and 50 or less.

If both the ratios A/B and C/D fall in the above-described ranges, namely, if the fat-soluble vitamin is distributed in the lengthwise direction as well as in the cross-sectional direction of the hollow-fiber membranes, the variation in the antioxidant performance can be suppressed, so that the hollow-fiber membrane blood purification device can exhibit a stable antioxidant performance.

On the basis of examinations made so far, it has been found that the water permeation performance of the hollow-fiber membrane blood purification device is degraded if the fat-soluble vitamin is immobilized on the hollow-fiber membranes. This problem can be generally overcome by raising the whole water permeation performance by changing the structure of the hollow-fiber membranes before immobilizing the fat-soluble vitamin, but the degree of the degradation in the water permeation performance is varied depending on the amount of the fat-soluble vitamin to be immobilized, and hence, it is necessary to produce and store hollow-fiber membranes having various water permeation performances, which largely increases the burden of the manufacturer.

In the hollow-fiber membrane blood purification device of the present embodiment, the water permeation performance can be controlled by selecting conditions for immobilizing the vitamin in the body end portion and the other divided sections of the hollow-fiber membrane bundle. Besides, as compared with a hollow-fiber membrane blood purification device in which the same amount of a fat-soluble vitamin as that in a body end portion is substantially uniformly distributed in the lengthwise direction, a higher water permeation performance can be attained with a substantially equivalent antioxidant performance kept.

<Solubility Parameter δ>

If the hydrophobic polymer of the present embodiment the affinity with the fat-soluble vitamin is preferably good so that the fat-soluble vitamin can be easily held on the hollow-fiber membranes. The solubility parameter δ is preferably 9.5 or more and 12.0 or less.

The solubility parameter δ corresponds to an index described in, for example, "Polymer Data Handbook, Fundamental edition" edited by The Society of Polymer Science, published by Baifukan Co., Ltd., first edition issued on Jan. 30, 1986, pp. 591-593, and a high solubility parameter means strong hydrophilicity and a low solubility parameter means strong hydrophobicity, and if a hydrophobic polymer having a solubility parameter within the aforementioned range is used, a prescribed amount of the fat-soluble vitamin is held on the hollow-fiber membranes.

Examples of the hydrophobic polymer includes polyethylene (8.4), polymethyl methacrylate (δ=9.10), polyarylate (9.3), a polymer alloy of polyethersulfone-polyarylate (9.6), polysulfone (δ=9.9), polyethersulfone (9.9), polyhydroxyethyl methacrylate (δ=10.0), cellulose diacetate (δ=11.4), polyacrylonitrile (δ=12.4), cellulose triacetate, and polycarbonate. It is noted that each value given above as δ is mentioned merely as an example.

As the hydrophobic polymer, these may be used singly or in combinations of two or more.

<Method for Producing Hollow-Fiber Membrane>

In the present embodiment, the hollow-fiber membrane can be produced by utilizing a known film forming technique.

The hydrophobic polymer and the hydrophilic polymer are dissolved in a common solvent to prepare a spinning dope.

The common solvent is not especially limited, and examples thereof include N,N-dimethylacetamide, dimethyl sulfoxide, N-methyl-2-pyrrolidone, dimethylformamide, sulfolane, acetone, dioxane, and a mixed solvent containing two or more of these solvents.

The spinning dope is continuously extruded into the shape of a hollow fiber and simultaneously coagulated by allowing it to come into contact with a coagulating agent, and thus, a continuous hollow-fiber membrane is obtained. The coagulating agent contains a mixed solution of a solvent for the hydrophobic polymer and a non-solvent, having a concentration of the solvent of 0% or more and 70% or less. Incidentally, for controlling a desired pore size of the hollow-fiber membrane, an additive such as water may be added to the spinning dope.

The concentration of the hydrophobic polymer in the spinning dope is not especially limited as long as a membrane can be formed and the resultant membrane can attain a performance as a permeable membrane, and is preferably 5% by mass or more and 35% by mass or less, and more preferably 10% by mass or more and 30% by mass or less. In order to attain a high water permeation performance, the concentration of the hydrophobic polymer is preferably lower, and further preferably 10% by mass or more and 25% by mass or less.

As for the concentration of the hydrophilic polymer based on the hydrophobic polymer in the spinning dope, a mixing ratio of the hydrophilic polymer based on 100% by mass of the hydrophobic polymer is preferably 27% by mass or less, more preferably 18% by mass or more and 27% by mass or less, and further preferably 20% by mass or more and 27% by mass or less.

If the mixing ratio of the hydrophilic polymer based on the hydrophobic polymer is 27% by mass or less, the amount of the hydrophilic polymer to be eluted preferably tends to be reduced. Besides, if it is 18% by mass or more, the concentration of the hydrophilic polymer on the surface of the hollow-fiber membrane is lowered, and the onset of leukopenia of abruptly lowering the leukocyte concentration in patient blood can be preferably reduced.

In the step of producing the hollow-fiber membrane, a double annular spinneret is used, and the spinning dope is discharged through a spinning nozzle, simultaneously with a hollow internal fluid used as the coagulating agent, from a tube into the air.

As the hollow internal fluid, water or a solution principally containing water can be used, and the composition and the like thereof can be determined in accordance with a desired water permeation performance of the hollow-fiber membrane. In general, a mixed solution of the common solvent used in the spinning dope and water is suitably used. In order to control the solute permeation performance of the membrane, the concentration of the common solvent is preferably controlled, and an aqueous solution of 0% by mass or more and 70% by mass or less is generally used. The hydrophilic polymer may be added to the hollow internal fluid to a content of 0% by mass or more and 2% by mass or less, so that the amount of the hydrophilic polymer present on the surface of the hollow-fiber membrane can be also controlled.

The spinning dope having been discharged through the spinning nozzle with the hollow internal fluid is allowed to pass through an idling section, introduced into and dipped in a coagulation bath principally containing water and disposed below the spinning nozzle so as to be completely coagulated, and after a washing step and the like, the thus obtained hollow-fiber membrane in a wet state is wound by a winder to obtain a bundle of the hollow-fiber membranes, and thereafter, the resultant is subjected to a drying step. Alternatively, after the washing step, the resultant may be dried in a drier to obtain a bundle of the hollow-fiber membranes.

A hollow-fiber membrane containing a polyolefin as the hydrophobic polymer can be produced by any known methods such as a wet phase transition method, a melting phase separation method, and a drawing opening method.

Among these methods, the drawing opening method is a method in which a crystalline polymer is molded into the shape of a hollow fiber or a film, cleavage is caused between crystalline lamellars by cold drawing, and a pore size is increased by hot drawing to obtain a porous structure, and in this method, a porous structure is produced by physical means of the drawing without adding an additive such as a solvent to a polymer material, and there does not arise a problem of residual solvent and the like, and therefore, this method can be suitably employed in the present embodiment for producing a hollow-fiber membrane containing a polyolefin.

Specifically, a hollow-fiber membrane is produced by spinning the polyolefin by using a double annular spinneret at a spinneret temperature of 145° C. or more and 155° C. or less, annealing the thus obtained hollow fiber at 115° C. or more and 120° C. or less for 1 hour or more and 3 hours or less, and hot drawing the resultant at room temperature or more and 100° C. or less by 10% or more and 30% or less, and subsequently at 100° C. or more and 120° C. or less by 30% or more and 350% or less.

If a polyolefin is used as the hydrophobic polymer, an ethylene-vinyl alcohol copolymer is preferably used as the hydrophilic polymer from the viewpoint of improving the blood compatibility by coating a pore surface of the hollow-fiber membrane.

An ethylene content in the ethylene-vinyl alcohol copolymer is preferably 20% by mole or more and 70% by mole or less, and more preferably 25% by mole or more and 50% by mole or less from the viewpoint of improving adhesiveness for preventing a coated layer from peeling off from the hollow-fiber membrane and from the viewpoint of the hydrophilicity.

The pore surface of the hollow-fiber membrane containing the polyolefin is treated with an ethylene-vinyl alcohol copolymer solution, and thus, the hollow-fiber membrane containing the hydrophobic polymer and the hydrophilic polymer can be obtained.

If the ethylene-vinyl alcohol copolymer solution contains a fat-soluble vitamin, the hollow-fiber membrane can be coated with the ethylene-vinyl alcohol copolymer and at the same time, the hollow-fiber membrane containing the fat-soluble vitamin can be obtained.

A bundle of the hollow-fiber membranes containing the ethylene-vinyl alcohol copolymer is obtained, and thereafter, the resultant is subjected to a drying treatment.

The ethylene-vinyl alcohol copolymer is dissolved in a water-miscible organic solvent.

The water-miscible organic solvent is not especially limited, and examples thereof include alcohols such as methanol, ethanol, n-propanol, isopropanol, n-butanol, t-butanol and cyclohexanol, polyhydric alcohols such as ethylene glycol, propylene glycol and glycerin, tetrahydrofuran, dioxane, dimethylformamide, dimethyl sulfoxide, dimethyl acetamide, formamide and ethylene chlorohydrin.

Among these, an organic solvent having a strong polarity is preferably used from the viewpoint of improving the adhesiveness to the polyolefin through localization of the ethylene-vinyl alcohol copolymer, and ethanol and acetone are preferred from the viewpoint of the solubility and low toxicity.

One of these organic solvents may be singly used, or any of these may be used as a mixed solvent. A mixed solvent with water is preferably used because the polarity is thus improved.

A ratio of water in the mixed solvent is not especially limited as long as the solubility of the ethylene-vinyl alcohol copolymer is not impaired, and the ratio can be appropriately set depending on the ethylene content in the copolymer, the temperature of the solution and the like. The ratio of water is, for example, preferably 5% by mass or more and 75% by mass or less.

The concentration of the copolymer to be used can be arbitrarily selected to be suitable for the coating, and is, for example, preferably 0.1% by mass or more and 5% by mass or less.

If a solution containing the fat-soluble vitamin is used, the concentration of the fat-soluble vitamin is preferably 0.01% by mass or more and 10% by mass or less, and more preferably 0.1% by mass or more and 5% by mass or less.

<Method for Producing Hollow-Fiber Membrane Blood Purification Device>

In a preferable method for producing the hollow-fiber membrane blood purification device of the present embodiment, for example, a bundle of hollow-fiber membranes is produced as described above, the bundle of the hollow-fiber membranes is inserted into a cylindrical vessel having a treatment liquid inlet/outlet port in contact with the outside of the hollow-fiber membranes, a potting agent of polyurethane or the like is injected into both ends of the bundle to form potting layers for sealing both the ends, and thereafter, an excessive portion of the potting agent having been cured is removed by cutting to open end surfaces, headers having a fluid inlet/outlet port are attached to the end surfaces, and a fat-soluble vitamin is then immobilized, and thus, the hollow-fiber membrane blood purification device is produced.

FIG. 3 illustrates a typical hollow-fiber membrane blood purification device, but the design may be appropriately changed within the scope of the object. In addition, the headers may be attached after immobilizing the fat-soluble vitamin.

A sterilization treatment step described later is preferably performed. The fat-soluble vitamin may be immobilized when the hollow-fiber membranes are in the shape of a bundle as described later.

<Step of Immobilizing Fat-Soluble Vitamin on Hollow-Fiber Membrane>

The hollow-fiber membrane blood purification device of the present embodiment may be produced by combining a direct dipping method and a coating method, for example, as those described in Production Examples 1 to 6 below, but the production method is not limited to the following.

Production Example 1

A portion of a bundle of hollow-fiber membranes corresponding to one body end portion of the hollow-fiber membrane bundle is directly dipped in a fat-soluble vitamin solution. After a prescribed time has elapsed, the hollow-fiber membranes are taken out of the solution. Subsequently, the solution remaining in the hollow-fiber membranes is blown away and dried by air blowing or the like from one end of the hollow-fiber membranes if necessary (air blowing step). If the air blowing is performed from the side having been dipped in the fat-soluble vitamin solution toward the other side not having been dipped, a small amount of the fat-soluble vitamin can be coated also on the side not having been dipped. The bundle may be dried without performing the air blowing step.

The thus obtained bundle of the hollow-fiber membranes is assembled, and thus, the hollow-fiber membrane blood purification device of the present embodiment can be obtained.

In the bundle of the hollow-fiber membranes before the dipping, hollow-fiber membranes in which the fat-soluble vitamin has not been immobilized at all may be used, or hollow-fiber membranes in which a given amount of the fat-soluble vitamin has been uniformly immobilized in the lengthwise direction by the coating method may be used, and when these methods are combined, the distribution of the fat-soluble vitamin in the lengthwise direction can be controlled.

In the present embodiment, the coating method refers to a method for obtaining a hollow-fiber membrane having a fat-soluble vitamin immobilized thereon by allowing a fat-soluble vitamin solution to pass through a hollow portion of the hollow fiber and then drying a solvent. Alternatively, after assembling the hollow-fiber membrane blood purification device, a coating solution of the fat-soluble vitamin may be further allowed to pass through the hollow-fiber membrane blood purification device.

The distribution of the fat-soluble vitamin in the lengthwise direction of the hollow-fiber membrane blood purification device can be controlled also in accordance with the concentration of the fat-soluble vitamin in the fat-soluble vitamin solution used for the dipping, the type of solvent, and a surfactant such as glycerin. One hollow-fiber membrane blood purification device has two body end portions, and if the amount of the fat-soluble vitamin to be immobilized is desired to be increased in both the two body end portions, the aforementioned method is practiced in both the body end portions.

When the fat-soluble vitamin is immobilized in at least one body end portion, the hollow-fiber membrane bundle as illustrated in FIG. 1 is obtained, and when the fat-soluble vitamin is immobilized in two body end portions, the hollow-fiber membrane bundle as illustrated in FIG. 2 can be obtained. Alternatively, the fat-soluble vitamin may be immobilized in different immobilized amounts in the two body end portions.

Production Example 2

A portion of a bundle of hollow-fiber membranes corresponding to one body end portion of the hollow-fiber membrane bundle is directly dipped in a fat-soluble vitamin solution. After a prescribed time has elapsed, the entire hollow-fiber membranes are further directly dipped in the fat-soluble vitamin solution. The hollow-fiber membranes are taken out of the fat-soluble vitamin solution, and the solution remaining in the hollow-fiber membranes is blown away and dried by the air blowing or the like from one end of the hollow-fiber membranes if necessary. In this case, since merely one of the body end portions is dipped in the fat-soluble vitamin solution for a relatively longer period of time, the amount of the fat-soluble vitamin immobilized in this body end portion is the largest. The bundle may be dried without performing the air blowing step.

The thus obtained bundle of the hollow-fiber membranes is assembled, and thus, the hollow-fiber membrane blood purification device of the present embodiment can be obtained.

In the bundle of the hollow-fiber membranes before the dipping, hollow-fiber membranes in which the fat-soluble vitamin has not been immobilized at all may be used, or hollow-fiber membranes in which a given amount of the fat-soluble vitamin has been uniformly immobilized in the lengthwise direction by the coating method may be used, and when these methods are combined, the distribution of the fat-soluble vitamin in the lengthwise direction can be controlled.

Alternatively, after assembling the hollow-fiber membrane blood purification device, a coating solution of the fat-soluble vitamin may be further allowed to pass through the hollow-fiber membrane blood purification device.

The distribution of the fat-soluble vitamin in the lengthwise direction of the hollow-fiber membrane blood purification device can be controlled also in accordance with the concentration of the fat-soluble vitamin in the fat-soluble vitamin solution used for the dipping, the type of solvent, and a surfactant such as glycerin. In Production Example 2, the concentration of the fat-soluble vitamin in the fat-soluble vitamin solution used for dipping the portion corresponding to the body end portion and the concentration of the fat-soluble vitamin in the fat-soluble vitamin solution used for dipping the whole hollow-fiber membranes can be changed, and therefore, the distribution of the fat-soluble vitamin in the lengthwise direction of the hollow-fiber membrane blood purification device can be controlled. Not only with respect to the concentration of the fat-soluble vitamin but also the type of solvent and the concentration and the type of surfactant, similar methods may be employed. One hollow-fiber membrane blood purification device has two body end portions, and if the amount of the fat-soluble vitamin to be immobilized is desired to be increased in both the two body end portions, the aforementioned method is practiced in both the body end portions.

When the fat-soluble vitamin is immobilized in at least one body end portion, the hollow-fiber membrane bundle as illustrated in FIG. 1 is obtained, and when the fat-soluble vitamin is immobilized in two body end portions, the hollow-fiber membrane bundle as illustrated in FIG. 2 can be obtained. Alternatively, the fat-soluble vitamin may be immobilized in different immobilized amounts in the two body end portions.

Production Example 3

A portion of a bundle of hollow-fiber membranes corresponding to one body end portion of the hollow-fiber membrane bundle is directly dipped in a fat-soluble vitamin solution. In this case, as the solvent used in the fat-soluble vitamin solution, a mixed solvent of a good solvent and a poor solvent for the fat-soluble vitamin, such as alcohol/water, is used, and the concentration of the good solvent (for example, alcohol) is set to a lowest concentration at which the fat-soluble vitamin can be dissolved. After a prescribed time has elapsed, the hollow-fiber membranes are taken out of the fat-soluble vitamin solution, or the entire hollow-fiber membranes are further directly dipped in the fat-soluble vitamin solution for a prescribed time and then taken out of the vitamin solution. The thus obtained hollow-fiber membranes are subjected to the air blowing or the like from one end of the hollow-fiber membranes for blowing away and drying the solution remaining in the hollow-fiber membranes if necessary. In this case, since merely the body end portion is dipped in the fat-soluble vitamin solution for a relatively longer period of time, and the concentration of the good solvent (for example, alcohol) is lowered to the lower limit concentration at which the fat-soluble vitamin can be dissolved, the fat-soluble vitamin is selectively immobilized on the hydrophobic polymer, and therefore, the amount of the fat-soluble vitamin immobilized in the body end portion is the largest. The bundle may be dried without performing the air blowing step.

The thus obtained bundle of the hollow-fiber membranes is assembled, and thus, the hollow-fiber membrane blood purification device of the present embodiment can be obtained.

In the bundle of the hollow-fiber membranes before the dipping, hollow-fiber membranes in which the fat-soluble vitamin has not been immobilized at all may be used, or hollow-fiber membranes in which a given amount of the fat-soluble vitamin has been uniformly immobilized in the lengthwise direction by the coating method may be used, and when these methods are combined, the distribution of the fat-soluble vitamin in the lengthwise direction can be controlled.

Alternatively, after assembling the hollow-fiber membrane blood purification device, a coating solution of the fat-soluble vitamin may be further allowed to pass through the hollow-fiber membrane blood purification device.

The distribution of the fat-soluble vitamin in the lengthwise direction of the hollow-fiber membrane blood purification device can be controlled also in accordance with the concentration of the fat-soluble vitamin in the fat-soluble vitamin solution used for the dipping, the types and the concentrations of the good solvent and the poor solvent, and the surfactant such as glycerin. In Production Example 3, since the composition of the fat-soluble vitamin solution used for dipping the portion corresponding to the body end portion and the composition of the fat-soluble vitamin solution of the fat-soluble vitamin solution used for dipping the whole hollow-fiber membranes can be changed, the distribution of the fat-soluble vitamin in the lengthwise direction of the hollow-fiber membrane blood purification device can be more precisely controlled.

One blood purification device has two body end portions, and if the amount of the fat-soluble vitamin to be immobilized is desired to be increased in both the two body end portions, the aforementioned method is practiced in both the body end portions. When the fat-soluble vitamin is immobilized in at least one body end portion, the hollow-fiber membrane bundle as illustrated in FIG. 1 is obtained, and when the fat-soluble vitamin is immobilized in two body end portions, the hollow-fiber membrane bundle as illustrated in FIG. 2 can be obtained. Alternatively, the fat-soluble vitamin may be immobilized in different immobilized amounts in the two body end portions.

Production Example 4

The bundle of the hollow-fiber membranes to which the fat-soluble vitamin is caused to adhere in the body end portion by each of the production methods of Production Examples 1 to 3 is assembled in a vessel, and the resultant is set in a coating device for the fat-soluble vitamin solution. The coating device includes, at a tip thereof, a jig having a pressure-resistant portion in an outer circumference thereof. The jig has a structure in close contact with the hollow-fiber membrane blood purification device, and the pressure-resistant portion may be in a mesh shape or a portion masking the whole circumference. The fat-soluble vitamin solution is supplied from the coating device to pass through the hollow-fiber membrane blood purification device at a flow rate of 100 mL/min or more and 1500 mL/min or less for 30 seconds or more and 100 seconds or less, and thereafter, the hollow-fiber membrane blood purification device is taken out. Subsequently, the fat-soluble vitamin solution remaining in the hollow-fiber membranes is blown away and dried by performing the air blowing or the like from one end of the hollow-fiber membrane blood purification device if necessary. At this point, if the air blowing is performed from the side coated with the fat-soluble vitamin solution, the fat-soluble vitamin solution can be moved also to the side not coated so as to coat the hollow-fiber membranes uniformly in the lengthwise direction. Alternatively, it may be dried with the coated side facing upward without performing the air blowing step. Caps are attached to the resultant, and thus, the hollow-fiber membrane blood purification device of the present embodiment can be obtained.

Production Example 5

The bundle of the hollow-fiber membranes to which the fat-soluble vitamin is caused to adhere in the body end portion by each of the production methods of Production Examples 1 to 3 is assembled in a vessel, and the resultant is set in a coating device for the fat-soluble vitamin solution. The coating device includes, at a tip thereof, a jig in close contact with the hollow-fiber membrane blood purification device. From the coating device, in which a tube for feeding the jig with the fat-soluble vitamin solution has an inner diameter $1/50$ times or more and $1/10$ times or less as large as the inner diameter of the hollow-fiber membrane bundle, the fat-soluble vitamin solution is allowed to pass through the hollow-fiber membrane blood purification device at a flow rate of 100 mL/min or more and 1500 mL/min or less for 30 seconds or more and 100 seconds or less, and thereafter, the hollow-fiber membrane blood purification device is taken out. Subsequently, the solution remaining in the hollow-fiber membranes is blown away and dried by performing the air blowing or the like from one end of the hollow-fiber membrane blood purification device if necessary. At this point, if the air blowing is performed from the side coated with the fat-soluble vitamin solution, the fat-soluble vitamin solution can be moved also to the side not coated so as to coat the hollow-fiber membranes uniformly in the lengthwise direction. Alternatively, it may be dried with the coated side facing upward without performing the air blowing step. Caps are attached to the resultant, and thus, the hollow-fiber membrane blood purification device of the present embodiment can be obtained.

Production Example 6

The bundle of the hollow-fiber membranes to which the fat-soluble vitamin is caused to adhere in the body end portion by each of the production methods of Production Examples 1 to 3 is assembled in a vessel, and the resultant is set in a coating device for the fat-soluble vitamin solution. The coating device has, at a tip thereof, a jig in close contact with the hollow-fiber membrane blood purification device. The fat-soluble vitamin solution is supplied from the coating device to pass through the hollow-fiber membrane blood purification device at a flow rate of 100 mL/min or more and 1500 mL/min or less for 30 seconds or more and 100 seconds or less, and thereafter, the hollow-fiber membrane blood purification device is taken out. Subsequently, if necessary, with a mask provided on the center portion, the fat-soluble vitamin solution remaining in the outside portion of the hollow-fiber membranes is blown away and dried by the air blowing or the like performed from one end of the hollow-fiber membrane blood purification device. Thereafter, the resultant is allowed to stand still for 1 hour or more and 12 hours or less, so that the center portion of the hollow-fiber membranes can be impregnated with the fat-soluble vitamin solution in the thickness direction, and thereafter, the mask provided on the center portion is removed, and the solution remaining in the hollow-fiber membranes is brown away and dried by the air blowing or the like. At this point, if the air blowing is performed from the side coated with the solution, the fat-soluble vitamin solution can be moved also to the side not coated so as to coat the hollow-fiber membranes uniformly in the lengthwise direction. Caps are attached to the resultant, and thus, the hollow-fiber membrane blood purification device of the present embodiment can be obtained.

After assembling the hollow-fiber membrane blood purification device, the coating solution of the fat-soluble vitamin may be further allowed to pass through the hollow-fiber membrane blood purification device.

The distribution of the fat-soluble vitamin in the lengthwise direction and the cross-sectional direction of the hollow-fiber membrane blood purification device can be controlled also in accordance with the concentration of the fat-soluble vitamin in the fat-soluble vitamin solution used for the coating, the type of solvent and the surfactant such as glycerin.

In each of Production Examples 1 to 6 of the present embodiment, the concentration of the fat-soluble vitamin in the fat-soluble vitamin solution is preferably 0.01% by mass or more and 10% by mass or less, and more preferably 0.1% by mass or more and 5% by mass or less. Besides, an additive (such as a surfactant) for making the fat-soluble vitamin soluble in an aqueous fat-soluble vitamin solution is preferably added in an amount $1/10$ times or more and twice or less as much as the fat-soluble vitamin.

As the solvent used in the fat-soluble vitamin solution, any of various solvents can be used, and an aqueous solution of alcohol such as propanol in a concentration of 50% by mass or more and 80% by mass or less is preferably used.

The time for dipping the hollow-fiber membranes in the fat-soluble vitamin solution in which the fat-soluble vitamin is dissolved in a concentration of 0.1% by mass or more and 2.0% by mass or less is preferably 30 seconds or more and 60 minutes or less, and more preferably 40 seconds or more and 10 minutes or less.

The fat-soluble vitamin solution is allowed to pass under conditions of a flow rate of 100 mL/min or more and 1500 mL/min or less for 30 seconds or more and 60 minutes or less, and preferably a flow rate of 300 mL/min or more and 1200 mL/min or less for 50 seconds or more and 10 minutes or less.

In each of Production Examples 1 to 6 of the present embodiment, as the bundle of the hollow-fiber membranes before the coating, hollow-fiber membranes in which the fat-soluble vitamin has not been immobilized at all may be used, hollow-fiber membranes in which a given amount of the fat-soluble vitamin has been uniformly immobilized in the cross-sectional direction by the coating method may be used, or a bundle of hollow-fiber membranes having different water permeation performances in the center portion and the outside portion may be used. When these methods are combined, the distribution of the fat-soluble vitamin in the lengthwise direction and the cross-sectional direction can be controlled.

<Step of Wetting Hollow-Fiber Membrane>

In the hollow-fiber membrane blood purification device having been assembled after immobilizing the fat-soluble vitamin, the hollow-fiber membranes may be wetted by an aqueous solution before sterilization. When the hollow-fiber membranes are wetted by an aqueous solution, the hollow-fiber membranes are stabilized, and are less changed in the performances such as the water permeation performance, dialysis performance and filtering performance. Examples of a method for wetting the hollow-fiber membranes by an aqueous solution include a method in which the aqueous solution is filled in the vessel filled with the hollow-fiber membranes, and a method in which the aqueous solution is filled in the vessel and then discharged. This step of wetting the hollow-fiber membranes can be performed also as a step of adding a sterilizing protective agent described below.

<Step of Adding Sterilizing Protective Agent>

A sterilizing protective agent is a radical scavenger having a plurality of hydroxyl groups or aromatic rings in one molecule to be used for protecting the hydrophilic polymer of the hollow-fiber membranes from being largely modified by radiation energy emitted in the sterilization treatment step described below.

Examples of the sterilizing protective agent include (poly-hydric) alcohols such as glycerin and propylene glycol, water-soluble sugars such as oligosaccharide and polysaccharide, and inorganic salts having an antioxidant action such as sulfite.

As a method for impregnating the hollow-fiber membranes with the sterilizing protective agent, a method in which the sterilizing protective agent is dissolved in an appropriate solvent to be introduced into the hollow-fiber membrane blood purification device, a method in which the sterilizing protective agent is dissolved in, for example, water or a physiological saline solution to be filled in a space within the hollow-fiber membrane blood purification device or to be impregnated into the hollow-fiber membranes alone, or the like is employed. In the wetting step, an aqueous solution containing the sterilizing protective agent may be used as the aqueous solution used for the wetting.

If the sterilizing protective agent is present in the hollow-fiber membrane blood purification device, the hollow-fiber membrane blood purification device, and the hollow-fiber membranes in particular, can be inhibited from being changed through a radiation sterilization treatment described later.

If the sterilizing protective agent is used in the form of a solution, the concentration of the sterilizing protective agent may be optimally determined in accordance with the material of the hollow-fiber membrane blood purification device, the type of hydrophilic polymer, and the conditions for the sterilization, and is preferably 0.001% by mass or more and 1% by mass or less, and more preferably 0.005% by mass or more and 0.5% by mass or less.

<Sterilization Treatment Step for Hollow-Fiber Membrane Blood Purification Device>

The hollow-fiber membrane blood purification device is preferably subjected to a sterilization treatment. Examples of a sterilization treatment method include radiation sterilization and steam sterilization.

Since a hollow-fiber membrane containing a large amount of a fat-soluble vitamin has a risk of damage when excessively heated, the radiation sterilization is more preferably performed. For the radiation sterilization, electron beams, γ-rays, X-rays or the like can be used. The exposure dose of the radiation is, in using γ-rays or electron beams, preferably 5 kGy or more and 50 kGy or less, and more preferably 20 kGy or more and 40 kGy or less.

EXAMPLES

The present invention will now be described in more detail with reference to examples, but it is noted that the present invention is not limited to the following examples. Measurement methods employed in the examples are as follows:

<Measurement of Amount of Fat-Soluble Vitamin Present in Hollow-Fiber Membranes of Divided Section of Hollow-Fiber Membrane Bundle>

A hollow-fiber membrane blood purification device was disassembled to take out hollow-fiber membranes, and the hollow-fiber membranes were divided into five sections for collecting hollow-fiber membranes of each of the divided sections. The thus obtained hollow-fiber membranes were washed with water and vacuum dried at 40° C. The dried hollow-fiber membranes were weighed out into a glass bottle so as to attain a hollow-fiber membrane inner surface area of 0.2 $m^2$, 80 mL of a 1% by mass Triton X-100 (Kishida Chemical Co., Ltd., for chemical use) aqueous solution was added thereto, and a fat-soluble vitamin was extracted at room temperature for 60 minutes under ultrasonic vibration. A quantitative determination operation is performed by liquid chromatography, and the amount of the fat-soluble vitamin in an extract was obtained by using a calibration curve obtained based on a peak area of a fat-soluble vitamin standard solution. Specifically, in the present embodiment, the amount of the fat-soluble vitamin corresponds to a value that can be obtained as an average among hollow-fiber membranes having a hollow-fiber inner surface area of 0.2 $m^2$.

A column (Shodex Asahipak ODP-506E packed column for HPLC) was attached to a high-performance liquid chromatograph (pump: Jasco Corporation PU-1580, detector: Shimadzu RID-6A, auto-injector: Shimadzu SIL-6B, data processor: Tosoh GPC-8020, column oven: GL Sciences 556), methanol for high-performance liquid chromatography used as a mobile phase was allowed to pass therethrough at a column temperature of 40° C. and a flow rate of 1 mL/min, and the concentration of the fat-soluble vitamin was obtained on the basis of an area of an absorption peak in an ultraviolet region. On the basis of the thus obtained concentration, the amount (mg/m$^2$) of the fat-soluble vitamin present in the hollow-fiber membranes of each divided section of the hollow-fiber membranes was obtained on the assumption that the extraction efficiency was 100%.

The amount of the fat-soluble vitamin partially oxidized through the sterilization treatment was also included in the amount of the fat-soluble vitamin per m$^2$ of the hollow-fiber membrane inner surface. For quantitatively determining the amount of the fat-soluble vitamin partially oxidized through the sterilization treatment, a fat-soluble vitamin to be precedently used for creating a calibration curve was exposed in the air to the radiation of 50 kGy to precedently determine an absorption peak of the partially oxidized fat-soluble vitamin, and the obtained absorption peak was included, for the addition, in peaks used for the area calculation.

<Measurement of Amounts of Fat-Soluble Vitamin Present in Center Portion and Outside Portion of Hollow-Fiber Membranes>

A hollow-fiber membrane blood purification device was disassembled to be divided into the center portion and the outside portion, and hollow-fiber membranes were collected from each of these portions, washed with water and vacuum dried at 40° C. The dried hollow-fiber membranes were weighed out into a glass bottle so as to attain a hollow-fiber membrane inner surface area of 0.2 m$^2$, 80 mL of a 1% by mass Triton X-100 (Kishida Chemical Co., Ltd., for chemical use) aqueous solution was added thereto, and a fat-soluble vitamin was extracted at room temperature for 60 minutes under ultrasonic vibration. A quantitative determination operation is performed by liquid chromatography, and the amount of the fat-soluble vitamin in an extract was obtained by using a calibration curve obtained based on a peak area of a fat-soluble vitamin standard solution. Specifically, in the present embodiment, the amount of the fat-soluble vitamin corresponds to a value that can be obtained as an average among hollow-fiber membranes having a hollow-fiber inner surface area of 0.2 m$^2$.

A column (Shodex Asahipak ODP-506E packed column for HPLC) was attached to a high-performance liquid chromatograph (pump: Jasco Corporation PU-1580, detector: Shimadzu RID-6A, auto-injector: Shimadzu SIL-6B, data processor: Tosoh GPC-8020, column oven: GL Sciences 556), methanol for high-performance liquid chromatography used as a mobile phase was allowed to pass therethrough at a column temperature of 40° C. and a flow rate of 1 mL/min, and the concentration of the fat-soluble vitamin was obtained on the basis of an area of an absorption peak in an ultraviolet region. On the basis of the thus obtained concentration, the amount (mg/m$^2$) of the fat-soluble vitamin present in the hollow-fiber membranes was obtained on the assumption that the extraction efficiency was 100%.

The amount of the fat-soluble vitamin partially oxidized through the sterilization treatment was also included in the amount of the fat-soluble vitamin per m$^2$ of the hollow-fiber membrane inner surface. For quantitatively determining the amount of the fat-soluble vitamin partially oxidized through the sterilization treatment, a fat-soluble vitamin to be precedently used for creating a calibration curve was exposed in the air to the radiation of 50 kGy to precedently determine an absorption peak of the partially oxidized fat-soluble vitamin, and the obtained absorption peak was included, for the addition, in peaks used for the area calculation.

<Measurement of Antioxidant Ability of Hollow-Fiber Membrane Blood Purification Device>

Ferric chloride hexahydrate was dissolved in pure water to prepare a 0.3 w/v % (an amount (g) of the solute in 100 mL of the solution) aqueous solution. Subsequently, a hollow-fiber membrane blood purification device was disassembled to collect hollow-fiber membranes, and the hollow-fiber membranes were washed with water and vacuum dried at 40° C. One g of the dried hollow-fiber membranes and 20 mL of the ferric chloride aqueous solution were weighed out into a glass bottle, the resultant was degassed at 60 mmHg for 10 minutes, and then incubated at 30° C. for 4 hours under shaking (and thus, a fat-soluble vitamin present in the hollow-fiber membranes reduced iron (III) ions to produce iron (II)). Then, 2.6 mL of the incubated aqueous solution, 0.7 mL of ethanol and 0.7 mL of a 0.5 w/v % 2,2'-bipyridyl ethanol aqueous solution separately prepared were mixed, and the resultant mixture was incubated at 30° C. for 30 minutes under shaking (and thus, the iron (II) and bipyridyl together formed a complex to develop a color). A spectrometer was used for measuring an absorbance at 520 nm of the solution thus colored.

Incubation, a color developing reaction and measurement of an absorbance similar to those described above were performed to create a calibration curve by using, instead of the hollow-fiber membranes, a fat-soluble vitamin ethanol solution having a known concentration, and antioxidant ability exhibited by 1 m$^2$ of the hollow-fiber membrane inner surface was obtained as a mass equivalent value of the fat-soluble vitamin (rounded off at the first decimal place).

If the mass equivalent value of the fat-soluble vitamin per m$^2$ of the hollow-fiber membrane inner surface was 15 (mg/m$^2$) or more, the antioxidant ability was determined to be good and evaluated as ○, and if it was less than 15 mg/m$^2$, the antioxidant ability was determined to be not good and evaluated as x.

Besides, in order to measure variation in the antioxidant performance, hollow-fiber membranes included in three hollow-fiber membrane type purification devices were subjected to the measurement under the same conditions to obtain a standard deviation. If the standard deviation was smaller than 10, the variation was determined to be small and evaluated as ○, and if it was 10 or more, it was determined that the antioxidant performance was not stable and evaluated as x.

<Measurement of Increase of Water Permeation Performance of Hollow-Fiber Membrane Blood Purification Device>

In both of a hollow-fiber membrane blood purification device produced in each of examples and comparative examples and a hollow-fiber membrane blood purification device (separately prepared) in which a fat-soluble vitamin, in the same amount as that in at least one body end portion where the amount of the fat-soluble vitamin was the largest in the former hollow-fiber membrane blood purification device, was substantially uniformly immobilized in the lengthwise direction, pure water was totally filtered through the hollow-fiber membrane blood purification devices under conditions of fixed pressure (200 mmHg) and temperature (37° C.), and a time required for the filtration was measured. On the basis of the result, the water permeation performance (UFR (mL/hr·mmHg)) was calculated.

Subsequently, increase of the water permeation performance was calculated in accordance with the following equation (1):

$$\text{Increase of water permeation performance}(UFR(\text{mL}/\text{hr}\cdot\text{mmHg})) = C - D \quad (1)$$

C: water permeation performance (UFR (mL/hr·mmHg)) of the hollow-fiber membrane blood purification device D: water permeation performance (UFR (mL/hr·mmHg)) of the hollow-fiber membrane blood purification device in which the fat-soluble vitamin in the same amount as in the body end portion was substantially uniformly immobilized in the lengthwise direction If the increase of the water permeation performance was larger, it was regarded and evaluated that the water permeation performance was high and the production rationality was high as compared with the blood purification device having the antioxidant performance at the same level, and if the increase of the water permeation performance is 10 (UFR (mL/hr·mmHg)) or more, the water permeation performance was determined to be good.

<Measurement of Lactate Dehydrogenase (LDH) Activity of Hollow-Fiber Membrane Blood Purification Device>

A hollow-fiber membrane blood purification device was disassembled for dividing hollow-fiber membranes to a center portion and an outside portion, and hollow-fiber membranes were randomly collected from the respective portions so that a ratio in number between the hollow-fiber membranes of the center portion and the hollow-fiber membranes of the outside portion could be 1:3. The lengths of the hollow-fiber membranes of a body end portion, where the amount of the fat-soluble vitamin was large, were adjusted to be within an effective length of 15 cm. Subsequently, a mini module was produced by bonding both ends of the hollow-fiber membranes to one another with an epoxy adhesive so that the hollow-fiber membrane inner surface area could be 50 mm². The mini module was washed by allowing 3 mL of a saline (Otsuka Pharmaceutical Co., Ltd., Otsuka normal saline) to pass through hollow portions of the hollow-fiber membranes at a flow rate of 0.6 mL/min.

Thereafter, 15 mL of heparinized human blood was controlled in temperature at 37° C. and was circulated through the mini module at a flow rate of 1.2 mL/min for 4 hours. After the circulation, the hollow portions of the mini module were washed with 10 mL of saline and the outside thereof was washed with 10 mL of saline.

From the washed mini module, the hollow-fiber membranes were collected, shred and put in a centrifuge tube for use in measurement of LDH activity, and the resultant was used as a measurement sample.

Next, 0.5 mL of a 0.5% by volume Triton X-100/PBS solution obtained by dissolving Triton X-100 (Nacalai Tesque) in a phosphate buffer solution (PBS) (Wako Pure Chemical Industries, Ltd.) was added to the centrifuge tube for use in the measurement of LDH, the resultant was centrifuged (at 2700 rpm for 5 min) to sink the hollow-fiber membranes in the solution, and the resultant was subjected to shaking extraction for 60 minutes to break cells (mainly platelets) adhering to the hollow-fiber membranes, and thus, LDH having been present in the cells was extracted. The thus obtained extract was dispensed in an amount of 0.05 mL, and 2.7 mL of a 0.6 mM sodium pyruvate solution and 0.3 mL of a 1.277 mg/mL nicotinamide adenine dinucleotide (NADH) solution were added thereto to cause a reaction, and after reacting the resultant at 37° C. for 1 hour, an absorbance at 340 nm was measured.

Similarly, hollow-fiber membranes not reacted with the blood (namely, blank) were also measured for the absorbance, and a difference in the absorbance was calculated in accordance with the following equation (2). Besides, a value obtained by dividing a value resulting from the following equation (2) by the hollow-fiber membrane inner surface area in accordance with the following equation (3) was obtained as LDH activity.

$$\Delta 340 \text{ nm} = \text{absorbance of sample obtained after reacting for 60 minutes} - \text{absorbance of blank obtained after reacting for 60 minutes} \quad (2)$$

$$\text{LDH activity} = \Delta 340 \text{ nm/hollow-fiber membrane inner surface area} \quad (3)$$

It was evaluated that a larger value calculated by the equation (3) means a larger amount of platelets adhering to the hollow-fiber membrane inner surface, and if the LDH activity of the hollow-fiber membrane blood purification device was 50 or less, it was evaluated to have good blood compatibility.

Example 1

As a spinning dope, 17.5% by mass of polysulfone (Solvay P-1700, solubility parameter δ of 9.9) and 3.5% by mass of polyvinylpyrrolidone (BASF K90) were dissolved in 79.0% by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 58.1% by mass of N,N-dimethylacetamide and 41.9% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%, an inner diameter of 185.0 μm and a thickness of 45.0 μm.

Next, a portion of the dried membranes including a substantially ⅕ portion (a body end portion) in the lengthwise direction was directly dipped in a coating solution obtained by dissolving 3.2% by mass of α-tocopherol (Wako Pure Chemical Industries, Ltd., special grade) used as a fat-soluble vitamin in a 57% by mass isopropanol aqueous solution. After 5 minutes, the whole hollow-fiber membranes were dipped in the coating solution further for 5 minutes. The hollow-fiber membranes were taken out of the coating solution, and the solvent was dried and removed by allowing dry air at 24° C. to pass therethrough for 30 minutes, and thus, the fat-soluble vitamin was immobilized on the hollow-fiber membranes by coating.

After immobilizing the fat-soluble vitamin, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened. A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 1.5 m².

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Example 2

As a spinning dope, 17.5% by mass of polysulfone (Solvay P-1700, solubility parameter δ of 9.9) and 3.5% by mass of polyvinylpyrrolidone (BASF K90) were dissolved in 79.0% by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 58.1% by mass of N,N-dimethylacetamide and 41.9% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%, an inner diameter of 185.0 μm and a thickness of 45.0 μm.

Next, a portion of the dried membranes including a substantially ⅕ portion (a body end portion) in the lengthwise direction was directly dipped in a coating solution obtained by dissolving 0.64% by mass of α-tocopherol (Wako Pure Chemical Industries, Ltd., special grade) used as a fat-soluble vitamin in a 57% by mass isopropanol aqueous solution. After 2 minutes, the hollow-fiber membranes were taken out of the coating solution, and subjected to the air blowing from the end of the hollow-fiber membranes on the side dipped in the isopropanol solution, so as to blow away the coating solution remaining in the membranes and to simultaneously apply the coating solution also onto a portion not dipped in the coating solution. The solvent was dried and removed by allowing dry air at 24° C. to pass therethrough for 30 minutes, and thus, the fat-soluble vitamin was immobilized on the hollow-fiber membranes by coating.

After immobilizing the fat-soluble vitamin, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened. A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 1.5 m².

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Example 3

A hollow-fiber membrane blood purification device was obtained in the same manner as in Example 1 except that a solution obtained by dissolving 0.21% by mass of α-tocopherol (Wako Pure Chemical Industries, Ltd., special grade) used as the fat-soluble vitamin in a 57% by mass isopropanol aqueous solution was used.

Example 4

In the hollow-fiber membranes obtained after immobilizing the fat-soluble vitamin in Example 3, a portion of the hollow-fiber membranes including the body end portion was further dipped in a coating solution obtained by dissolving 3.2% by mass of α-tocopherol (Wako Pure Chemical Industries, Ltd., special grade) used as the fat-soluble vitamin in a 57% by mass isopropanol aqueous solution. After 1 minute, the hollow-fiber membranes were taken out of the coating solution, and subjected to the air blowing from the end on the side opposite to the side dipped in the coating solution for blowing away the coating solution remaining in the membranes. Dry air at 24° C. was allowed to pass therethrough for 30 minutes to remove the solvent by drying, and thus, the fat-soluble vitamin was immobilized on the hollow-fiber membranes by coating.

After immobilizing the fat-soluble vitamin, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened.

A coating solution obtained by dissolving 1.1% by mass of α-tocopherol (Wako Pure Chemical Industries, Ltd., special grade) used as the fat-soluble vitamin in a 57% by mass isopropanol aqueous solution was prepared in a coating device. The hollow-fiber membranes obtained as described above were set in the coating device equipped with a jig having a pressure-resistant portion in an outer circumference thereof, and the coating solution was allowed to pass, from the coating device, through the hollow-fiber membranes at a flow rate of 500 mL/min for 30 seconds, and then, the hollow-fiber membranes were taken out. Dry air at 35° C. was allowed to pass therethrough for 30 minutes from the end of the hollow-fiber membranes on the side for allowing the coating solution to pass, so as to remove the solvent by drying, and thus, the fat-soluble vitamin was immobilized by coating.

A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 1.5 m².

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Example 5

As a spinning dope, 17.5% by mass of polysulfone (Solvay P-1700, solubility parameter δ of 9.9) and 3.5% by mass of polyvinylpyrrolidone (BASF K90) were dissolved in 79.0% by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 58.1% by mass of N,N-dimethylacetamide and 41.9% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%, an inner diameter of 185.0 µm and a thickness of 45.0 µm.

Next, a portion of the dried membranes including a substantially ⅕ portion (a body end portion) in the lengthwise direction was directly dipped in a coating solution obtained by dissolving 0.64% by mass of α-tocopherol (Wako Pure Chemical Industries, Ltd., special grade) used as a fat-soluble vitamin in a 57% by mass isopropanol aqueous solution. After 1 minute, the whole hollow-fiber membranes were dipped in the coating solution further for 1 minute. The hollow-fiber membranes were taken out of the coating solution, and the solvent was dried and removed by allowing dry air at 24° C. to pass therethrough for 30 minutes, and thus, the fat-soluble vitamin was immobilized on the hollow-fiber membranes by coating. Subsequently, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened.

A coating solution obtained by dissolving 1.2% by mass of α-tocopherol (Wako Pure Chemical Industries, Ltd., special grade) used as the fat-soluble vitamin in a 57% by mass isopropanol aqueous solution was prepared in a coating device. The hollow-fiber membranes obtained as described above were set in the coating device, and the coating solution was allowed to pass through the hollow-fiber membranes at a flow rate of 1500 mL/min for 10 seconds, and then the hollow-fiber membranes were taken out. A tube for feeding the coating solution had an inner diameter 1/40 times as large as the inner diameter of the hollow-fiber membrane bundle. Dry air at 35° C. was allowed to pass therethrough for 30 minutes from the end of the hollow-fiber membranes on the side for allowing the coating solution to pass, so as to remove the solvent by drying, and thus, the fat-soluble vitamin was immobilized on the hollow-fiber membranes by coating.

A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 1.5 m².

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Example 6

As a spinning dope, 17.5% by mass of polysulfone (Solvay P-1700, solubility parameter δ of 9.9) and 3.5% by mass of polyvinylpyrrolidone (BASF K90) were dissolved in 79.0% by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 58.1% by mass of N,N-dimethylacetamide and 41.9% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%, an inner diameter of 185.0 µm and a thickness of 45.0 µm.

Next, a portion of the dried membranes including a substantially ⅕ portion (a body end portion) in the lengthwise direction was directly dipped in a coating solution obtained by dissolving 1.7% by mass of α-tocopherol (Wako Pure Chemical Industries, Ltd., special grade) used as a fat-soluble vitamin in a 57% by mass isopropanol aqueous solution. After 30 seconds, the hollow-fiber membranes were taken out of the coating solution, and subjected to the air blowing from the end of the hollow-fiber membranes on the side dipped in the coating solution, so as to blow away the coating solution remaining in the membranes and to simultaneously apply the coating solution onto a portion not dipped in the coating solution. Dry air at 24° C. was allowed to pass therethrough for 30 minutes, so as to remove the solvent by drying, and thus, the fat-soluble vitamin was immobilized on the hollow-fiber membranes by coating.

After immobilizing the fat-soluble vitamin, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened.

A coating solution obtained by dissolving 1.3% by mass of α-tocopherol (Wako Pure Chemical Industries, Ltd., special grade) used as the fat-soluble vitamin in a 57% by mass isopropanol aqueous solution was prepared in a coating device. The hollow-fiber membranes obtained as described above were set in the coating device quipped with a jig having a pressure-resistant portion in an outer circumference thereof, and the coating solution was allowed to pass, from the coating device, through the hollow-fiber membranes at a flow rate of 500 mL/min for 2 minutes, and then, the hollow-fiber membranes were taken out. A tube for feeding the coating solution had an inner diameter 1/10 times as large as the inner diameter of the hollow-fiber membrane bundle. Dry air at 35° C. was allowed to pass therethrough for 30 minutes from the end of the hollow-fiber membranes on the side for allowing the coating solution to pass, so as to remove the solvent by drying, and thus, the fat-soluble vitamin was immobilized by coating.

A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 1.5 m².

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Example 7

As a spinning dope, 17.5% by mass of polysulfone (Solvay P-1700, solubility parameter δ of 9.9) and 3.5% by mass of polyvinylpyrrolidone (BASF K90) were dissolved in 79.0% by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 58.1% by mass of N,N-dimethylacetamide and 41.9% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%, an inner diameter of 185.0 μm and a thickness of 45.0 μm.

Next, a portion of the dried membranes including a substantially ⅕ portion (a body end portion) in the lengthwise direction was directly dipped in a coating solution obtained by dissolving 2.2% by mass of α-tocopherol (Wako Pure Chemical Industries, Ltd., special grade) used as a fat-soluble vitamin in a 57% by mass isopropanol aqueous solution. After 1 minute, the hollow-fiber membranes were taken out of the coating solution, and subjected to the air blowing from the end of the hollow-fiber membranes on the side dipped in the coating solution, so as to blow away the coating solution remaining in the membranes and to simultaneously apply the coating solution onto a portion not dipped in the coating solution. Dry air at 24° C. was allowed to pass therethrough for 30 minutes, so as to remove the solvent by drying, and thus, the fat-soluble vitamin was immobilized on the hollow-fiber membranes by coating.

After immobilizing the fat-soluble vitamin, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened. A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 1.5 m².

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Example 8

As a spinning dope, 17.5% by mass of polysulfone (Solvay P-1700, solubility parameter δ of 9.9) and 3.5% by mass of polyvinylpyrrolidone (BASF K90) were dissolved in 79.0% by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 58.1% by mass of N,N-dimethylacetamide and 41.9% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%, an inner diameter of 185.0 μm and a thickness of 45.0 μm.

Next, a portion of the dried membranes including a substantially ⅕ portion (a body end portion) in the lengthwise direction was directly dipped in a coating solution obtained by dissolving 3.2% by mass of α-tocopherol (Wako Pure Chemical Industries, Ltd., special grade) used as a fat-soluble vitamin in a 57% by mass isopropanol aqueous solution. After 5 minutes, the whole hollow-fiber membranes were dipped in the coating solution further for 3 minutes. The hollow-fiber membranes were taken out of the coating solution, and the solvent was dried and removed by allowing dry air at 24° C. to pass therethrough for 30 minutes, and thus, the fat-soluble vitamin was immobilized on the hollow-fiber membranes by coating. Subsequently, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened.

A coating solution obtained by dissolving 1.6% by mass of α-tocopherol (Wako Pure Chemical Industries, Ltd., special grade) used as the fat-soluble vitamin in a 57% by mass isopropanol aqueous solution was prepared in a coating device. The hollow-fiber membranes obtained as described above were set in the coating device equipped with a jig having a pressure-resistant portion in an outer circumference thereof, and the coating solution was allowed to pass, from the coating device, through the hollow-fiber membranes at a flow rate of 500 mL/min for 30 seconds, and then, the hollow-fiber membranes were taken out. Dry air at 35° C. was allowed to pass therethrough for 30 minutes from the end of the hollow-fiber membranes on the side for allowing the coating solution to pass, so as to remove the solvent by drying, and thus, the fat-soluble vitamin was immobilized on the hollow-fiber membranes by coating.

A header cap having a nozzle for inlet (outlet) of blood was attached to each of the end portions, the resultant was subjected to a sterilization treatment by performing a wetting step in the same manner as in Example 1, and thus, the hollow-fiber membranes were assembled into the shape of a hollow-fiber membrane blood purification device having a hollow-fiber membrane inner surface area of 1.5 m².

Example 9

A hollow-fiber membrane blood purification device was obtained in the same manner as in Example 7 except that a coating solution obtained by dissolving 3.2% by mass of α-tocopherol (Wako Pure Chemical Industries, Ltd., special grade) used as the fat-soluble vitamin in a 57% by mass isopropanol aqueous solution was used.

Example 10

A hollow-fiber membrane blood purification device was obtained in the same manner as in Example 3 except that the time for directly dipping a portion of the dried membranes including substantially the ⅕ portion (body end portion) in the lengthwise direction in α-tocopherol (Wako Pure Chemical Industries, Ltd., special grade) was changed to 40 seconds and the hollow-fiber membrane inner surface area was changed to 2.5 m².

Example 11

As a spinning dope, 17.5% by mass of polysulfone (Solvay P-1700, solubility parameter δ of 9.9) and 3.5% by mass of polyvinylpyrrolidone (BASF K90) were dissolved in 79.0% by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 58.1% by mass of N,N-dimethylacetamide and 41.9% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%, an inner diameter of 185.0 μm and a thickness of 45.0 μm.

Next, a portion of the dried membranes including a substantially ⅕ portion (a body end portion) in the lengthwise direction was directly dipped in a coating solution obtained by dissolving 3.2% by mass of α-tocopherol (Wako Pure Chemical Industries, Ltd., special grade) used as a fat-soluble vitamin in a 57% by mass isopropanol aqueous solution. After 5 minutes, the whole hollow-fiber membranes were dipped in the coating solution further for 1 minute. The hollow-fiber membranes were taken out of the coating solution, and the solvent was dried and removed by allowing dry air at 24° C. to pass therethrough for 30 minutes, and thus, the fat-soluble vitamin was immobilized on the hollow-fiber membranes by coating.

After immobilizing the fat-soluble vitamin, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened.

A coating solution obtained by dissolving 1.6% by mass of α-tocopherol (Wako Pure Chemical Industries, Ltd., special grade) used as the fat-soluble vitamin in a 57% by mass isopropanol aqueous solution was prepared in a coating device. The hollow-fiber membranes obtained as described above were set in the coating device equipped with a jig having a pressure-resistant portion in an outer circumference thereof, and the coating solution was allowed to pass, from the coating device, through the hollow-fiber membranes at a flow rate of 500 mL/min for 10 seconds, and then, the hollow-fiber membranes were taken out. Dry air at 35° C. was allowed to pass therethrough for 30 minutes from the end of the hollow-fiber membranes on the side for allowing the coating solution to pass, so as to remove the solvent by drying, and thus, the fat-soluble vitamin was immobilized by coating.

A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 2.5 m².

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Example 12

A hollow-fiber membrane blood purification device was obtained in the same manner as in Example 4 except that the concentration of the aqueous solution of the fat-soluble vitamin for directly dipping the portion of the dried membranes including substantially the ⅕ portion (body end portion) in the lengthwise direction first was changed to a coating solution obtained by dissolving 2.5% by mass of α-tocopherol (Wako Pure Chemical Industries, Ltd., special grade) used as the fat-soluble vitamin in a 57% by mass isopropanol aqueous solution, and that the hollow-fiber membrane inner surface area was changed to 2.5 m².

Example 13

In the hollow-fiber membranes obtained after immobilizing the fat-soluble vitamin in Example 3, a portion of the hollow-fiber membranes including the body end portion was further dipped in a coating solution obtained by dissolving 3.0% by mass of α-tocopherol (Wako Pure Chemical Industries, Ltd., special grade) used as the fat-soluble vitamin in a 57% by mass isopropanol aqueous solution. After 1 minute, the hollow-fiber membranes were taken out of the coating solution, and subjected to the air blowing from the end of the hollow-fiber membranes opposite to the side dipped in the coating solution, so as to blow away the coating solution remaining in the membranes, and dry air at 24° C. was allowed to pass therethrough for 30 minutes, so as to remove the solvent by drying, and thus, the fat-soluble vitamin was immobilized on the hollow-fiber membranes by coating.

After immobilizing the fat-soluble vitamin, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened.

A coating solution obtained by dissolving 3.2% by mass of α-tocopherol (Wako Pure Chemical Industries, Ltd., special grade) used as the fat-soluble vitamin in a 57% by mass isopropanol aqueous solution was prepared in a coating device. The hollow-fiber membranes obtained as described above were set in the coating device equipped with a jig having a pressure-resistant portion in an outer circumference thereof, and the coating solution was allowed to pass, from the coating device, through the hollow-fiber membranes at a flow rate of 500 mL/min for 25 seconds, and then, the blood treatment device was taken out. Dry air at 35° C. was allowed to pass therethrough for 30 minutes from the end of the hollow-fiber membranes on the side for allowing the coating solution to pass, so as to remove the solvent by drying, and thus, the fat-soluble vitamin was immobilized on the hollow-fiber membranes by coating.

A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 2.5 m².

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Example 14

A hollow-fiber membrane blood purification device was obtained in the same manner as in Example 1 except that a coating solution obtained by dissolving 0.7% by mass of α-tocopherol (Wako Pure Chemical Industries, Ltd., special grade) used as the fat-soluble vitamin in a 57% by mass isopropanol aqueous solution was used.

Example 15

A spinning dope containing 17.5% by mass of polyethersulfone (Sumitomo Chemical Co., Ltd., 4800P, solubility parameter δ of 9.9), 3.5% by mass of polyvinylpyrrolidone (BASF K90), 31.2% by mass of triethylene glycol (manufactured by Mitsubishi Chemical Corporation), 1.0% by mass of water used as a non-solvent, and 46.8% by mass of dimethylacetamide (manufactured by Mitsui Chemicals Inc.) was kept at 45° C., discharged through a double annular spinneret together with a hollow internal fluid of water, allowed to pass through an air gap of 600 mm and dipped in a coagulation bath containing water, and then wound into a fiber bundle at 60 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%.

Thereafter, the resultant membranes were washed with pure water at 45° C. for 1 minute and pure water at 80° C. for 90 seconds, and then skeined, and thus, hollow-fiber membranes having an inner diameter of 199.0 μm and a thickness of 29.5 μm were obtained.

A hollow-fiber membrane blood purification device was obtained in the same manner as in Example 2 except that a solution obtained by dissolving 0.7% by mass of α-tocopherol (Wako Pure Chemical Industries, Ltd., special grade) used as the fat-soluble vitamin in a 57% by mass isopropanol aqueous solution was used in the method for immobilizing the fat-soluble vitamin, and that the hollow-fiber membrane inner surface area was changed to 2.5 m².

Example 16

As a spinning dope, 15% by mass of polyarylate (Unitika U polymer, solubility parameter δ of 9.3) and 15% by mass of polyethersulfone (Sumitomo Chemical Co., Ltd., Sumika Excel PES, solubility parameter δ of 9.9) were dissolved in 70% by mass of N-methyl pyrrolidone to obtain a homogeneous solution.

The obtained spinning dope was kept at 60° C., discharged through a double annular spinneret together with a hollow internal fluid of a mixed solution obtained by dissolving 0.5% by mass of polyvinylpyrrolidone (BASF Kollidon K-90) in 19.5% by mass of N-methyl pyrrolidone and 80.0% by mass of water, allowed to pass through an air gap of 0.9 m and dipped in a coagulation bath at 50° C. containing 19.5% by mass of N-methyl pyrrolidone and 80.5% by mass of water, and then wound into a fiber bundle at 700 m/min. After cutting the thus wound fiber bundle, the bundle was washed with water so as to remove the solvent remaining in the membranes, and the resultant membranes were dried with dry air at 35° C. to obtain dried membranes having an inner diameter of 210 μm and a thickness of 30 μm.

A hollow-fiber membrane blood purification device of the present invention was obtained in the same manner as in Example 2 except that a solution obtained by dissolving 1.0% by mass of α-tocopherol (Wako Pure Chemical Industries, Ltd., special grade) used as the fat-soluble vitamin in a 57% by mass isopropanol aqueous solution was used in the method for immobilizing the fat-soluble vitamin, and that the hollow-fiber membrane inner surface area was changed to 2.1 m².

Example 17

As a spinning dope, 125 g of syn-PMMA having a weight average molecular weight of 400,000 and 25 g of iso-PMMA having a weight average molecular weight of 500,000 were dissolved in 150 g of glycerin and 1200 g of dimethyl sulfoxide with stirring at 125° C. for 18 hours, and the resultant was allowed to stand still for degassing to obtain a homogeneous solution.

The thus obtained spinning dope was discharged, by using a gear pump, from a hopper at 120° C. at a rate of 5.3 g/min into the air through a hollow fiber nozzle at a nozzle temperature of 60° C. Simultaneously, a hollow internal fluid of a mixed solution of 70% by mass of dimethyl sulfoxide and 30% by mass of water was injected at a rate of 1.65 mL/min. Subsequently, the resultant was dipped in a coagulation bath at 60° C. containing a 5% dimethyl sulfoxide aqueous solution, and washed with water, and the resultant hollow-fiber membranes were impregnated with a 63% by mass glycerin aqueous solution used as a humectant. The resultant was subjected to a heat treatment bath at 85° C. for removing excessive glycerin, and was wound at 60 m/min with a spacer yarn wound. The thus wound bundle was cut to obtain a hollow fiber bundle. The thus obtained hollow-fiber membranes had an inner diameter of 200 μm and a thickness of 30 μm.

A hollow-fiber membrane blood purification device of the present invention was obtained in the same manner as in Example 2 except that a solution obtained by dissolving 0.6% by mass of α-tocopherol (Wako Pure Chemical Industries, Ltd., special grade) used as the fat-soluble vitamin and 10% by mass of glycerin in a 57% by mass isopropanol aqueous solution was used in the method for immobilizing the fat-soluble vitamin, and that the hollow-fiber membrane inner surface area was changed to 1.6 m².

Example 18

High density polyethylene (having a density of 0.988, Mu value 5.5, HI-ZEX 2208J, having a solubility parameter δ of 8.40) was spun by using a double annular spinneret at a spinneret temperature of 150° C. to obtain a hollow fiber.

The obtained hollow fiber was subjected to an annealing treatment at 120° C. for 2 hours, and then to the hot drawing at room temperature by 30% and subsequently at 105° C. by 350% to obtain hollow-fiber membranes. The hollow-fiber membranes had an inner diameter of 300 μm and a thickness of 45 μm.

An ethylene-vinyl alcohol copolymer having an ethylene content of 38% by mole (Nippon Synthetic Chemical Industry Co., Ltd., Soarnol E) was dissolved, by heating, in a 75% by mass acetone aqueous solution to obtain a 0.5% by mass solution. A portion of the hollow-fiber membranes including a substantially ⅕ portion in the lengthwise direction (body end portion) was directly dipped for 5 minutes in a coating solution obtained by dissolving, in the above-described solution, 0.9% by mass of α-tocopherol (Wako Pure Chemical Industries, Ltd., special grade) used as the fat-soluble vitamin. Next, the whole hollow-fiber membranes were dipped for 3 minutes in the 0.5% by mass solution obtained by dissolving, by heating, in the ethylene-vinyl alcohol copolymer having an ethylene content of 38% by mole (Nippon Synthetic Chemical Industry Co., Ltd., Soarnol E) in a 75% by mass acetone aqueous solution. After removing an excessive portion of the copolymer solution, the resultant was dried with hot air at 40° C. for 3 hours.

After immobilizing the fat-soluble vitamin, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened. A header cap having a nozzle for inlet (outlet) of blood was attached to each of the end portions, and thus, the hollow-fiber membranes were assembled into the shape of a hollow-fiber membrane blood purification device having a membrane area of 1.6 m².

Example 19

As a spinning dope, 17.5% by mass of polysulfone (Solvay P-1700, solubility parameter δ of 9.9) and 3.5% by mass of polyvinylpyrrolidone (BASF K90) were dissolved in 79.0% by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 58.1% by mass of N,N-dimethylacetamide and 41.9% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%, an inner diameter of 185.0 μm and a thickness of 45.0 μm.

Next, a portion of the dried membranes including a substantially ⅕ portion (a body end portion) in the lengthwise direction was directly dipped in a coating solution obtained by dissolving 0.64% by mass of α-tocopherol (Wako Pure Chemical Industries, Ltd., special grade) used as a fat-soluble vitamin in a 57% by mass isopropanol aqueous solution. After 2 minutes, the hollow-fiber membranes were taken out of the coating solution. Subsequently, a portion of the dried membranes including the other ⅕ portion (a body end portion) was directly dipped in the coating solution. After 2 minutes, the hollow-fiber membranes were subjected to the air blowing from the end on the side dipped lastly in the coating solution, so as to blow away the coating solution remaining in the membranes and to simultaneously apply the coating solution also onto a portion not dipped in the coating solution. Dry air at 24° C. was allowed to pass therethrough for 30 minutes to remove the solvent by drying, and thus, the fat-soluble vitamin was immobilized on the hollow-fiber membranes by coating.

After immobilizing the fat-soluble vitamin, the hollow-fiber membranes were filled in a cylindrical vessel having two nozzles for inlet and outlet of a liquid, both ends thereof were embedded with a urethane resin, and a cured urethane portion was cut to obtain an end portion where the hollow-fiber membranes were opened. A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 1.5 m².

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Comparative Example 1

As a spinning dope, 17.5% by mass of polysulfone (Solvay P-1700, solubility parameter δ of 9.90) and 3.5% by mass of polyvinylpyrrolidone (BASF K90) were dissolved in 79.0% by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 58.1% by mass of N,N-dimethylacetamide and 41.9% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%.

The dried membranes were filled in a cylindrical vessel having two nozzles for inlet and outlet of a liquid, both ends thereof were embedded with a urethane resin, and a cured urethane portion was cut to obtain an end portion where the hollow-fiber membranes were opened. A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 1.5 m².

Next, a coating solution obtained by dissolving 3.5% by mass of α-tocopherol (Wako Pure Chemical Industries, Ltd., special grade) in a 57% by mass isopropanol aqueous solution was allowed to pass through hollow portions of the hollow-fiber membranes at 24° C. for 1 minute from a blood inlet nozzle of the hollow-fiber membrane blood purification device to bring the α-tocopherol into contact with the hollow-fiber membranes. At this point, a tube for feeding the coating solution had an inner diameter ⅕ times as large as the inner diameter of the hollow-fiber membrane bundle.

Thereafter, the solution remaining in the hollow portions was removed by the air blowing, dry air at 24° C. under an isopropanol atmosphere was allowed to pass therethrough for 30 minutes to remove the solvent by drying, and thus, the α-tocopherol was immobilized on the hollow-fiber membranes.

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Comparative Example 2

A hollow-fiber membrane blood purification device was obtained in the same manner as in Comparative Example 1 except that the concentration of the α-tocopherol in the coating solution was changed to 0.16% by mass.

Comparative Example 3

A hollow-fiber membrane blood purification device was obtained on the basis of contents described in Example 1 of Japanese Patent Laid-Open No. 2006-296931 specifically as follows.

As a spinning dope, 18.0% by mass of polysulfone (Solvay P-1700, solubility parameter δ of 9.90) and 4.3% by mass of polyvinylpyrrolidone (BASF K90) were dissolved in 77.7% by mass of N,N-dimethylacetamide to obtain a homogeneous solution. A mixing ratio of the polyvinylpyrrolidone to the polysulfone in the spinning dope was 24% by mass.

The obtained spinning dope was kept at 60° C., discharged through a double annular spinneret together with a hollow internal fluid of a mixed solution of 30% by mass of N,N-dimethylacetamide and 70% by mass of water, allowed to pass through an air gap of 0.96 m and dipped in a coagulation bath containing water at 75° C., and then wound into a fiber bundle at 80 m/min. After cutting the thus wound fiber bundle, the bundle was washed with a hot water shower at 80° C. supplied from above the cut cross-section of the bundle over 2 hours so as to remove the solvent remaining in the membranes, and the resultant membranes were dried to obtain dried membranes having a water content less than 1%.

The dried membranes were filled in a cylindrical vessel having two nozzles for inlet and outlet of a liquid, both ends thereof were embedded with a urethane resin, and a cured urethane portion was cut to obtain an end portion where the hollow-fiber membranes were opened. A header cap having a nozzle for inlet (outlet) of blood was attached to each of the end portions, and thus, the hollow-fiber membranes were assembled into the shape of a hollow-fiber membrane blood purification device having a hollow-fiber membrane inner surface area of 1.5 m².

Next, a coating solution obtained by dissolving 0.23% by mass of α-tocopherol (Wako Pure Chemical Industries, Ltd., special grade) in a 57% by mass isopropanol aqueous solution was allowed to pass through hollow portions of the hollow-fiber membranes for 52 seconds from the blood inlet nozzle of the hollow-fiber membranes to bring the α-tocopherol into contact with the hollow-fiber membranes. Besides, after removing the solution remaining in the hollow portions by air flushing, dry air at 24° C. was allowed to pass therethrough for 30 minutes to remove the solvent by drying, and thus, the hollow-fiber membranes were coated with the α-tocopherol.

As a wetting step, an aqueous solution containing 0.06% by mass of sodium pyrosulfite used as a sterilizing protective agent and 0.03% by mass of sodium carbonate used for pH control was filled in a blood-side passage and a filtrate-side passage of the hollow-fiber membrane blood purification device, and with the nozzles tightly stopped, the resultant was irradiated for sterilization with γ-rays at 25 kGy, and in this manner, a hollow-fiber membrane blood purification device was obtained.

Comparative Example 4

A hollow-fiber membrane blood purification device was obtained on the basis of contents described in Example 2 of Japanese Patent Laid-Open No. 2013-9761 specifically as follows.

As a spinning dope, 17.0% by mass of polysulfone (Solvay P-1700, solubility parameter δ of 9.90), 4.0% by mass of polyvinylpyrrolidone (BASF K90) and 0.5 parts by mass of α-tocopherol (Wako Pure Chemical Industries, Ltd., special grade) were dissolved in 78.5 parts by mass of N,N-dimethylacetamide to obtain a homogeneous solution. A mixing ratio of the polyvinylpyrrolidone to the polysulfone in the spinning dope was 20% by mass.

The obtained spinning dope was kept at 60° C., discharged through a double annular spinneret together with a hollow internal fluid of a mixed solution of 42.0% by mass of N,N-dimethylacetamide and 58.0% by mass of water, allowed to pass through an air gap of 0.5 m and dipped in a coagulation bath containing water at 60° C., allowed to pass through a coagulating step and a water washing step (a water washing treatment) at a rate of 30 m/min, and then introduced into a dryer for drying at 120° C. for 2 minutes, and further subjected to a heat treatment at 160° C. for 0.5 minutes, and thereafter, the resultant polysulfone-based hollow-fiber membrane provided with crimps was wound.

A bundle of 10000 hollow-fiber membranes thus wound was filled in a plastic cylindrical vessel designed to attain a hollow-fiber membrane inner surface area of 1.5 m², both ends thereof were adhesively fixed with a urethane resin, and were cut to obtain end portions where the hollow-fiber membranes were opened.

One hundred mL of an aqueous solution containing 95 parts by mass of distilled water (Otsuka Pharmaceutical Co., Ltd.) and 5 parts by mass of glycerin (Wako Pure Chemical Industries, Ltd., special grade) was allowed to pass through the hollow fiber membranes, and the resultant was blown with air at 0.3 MPa for 10 seconds. Subsequently, the resultant was dried with dry air at 40° C. for 1 hour. After drying, header caps were attached to both the ends. After stopping blood inlet/outlet nozzles, electron beams were irradiated at 20 kGy, and thus, a hollow-fiber membrane blood purification device was obtained.

TABLE 1

|   | Example 1 | Example 2 | Example 3 | Example 4 | Example 5 | Example 6 | Example 7 | Example 8 | Example 9 | Example 10 | Example 11 | Example 12 |
|---|---|---|---|---|---|---|---|---|---|---|---|---|
| A: Amount (mg/m²) of fat-soluble vitamin per m² of hollow-fiber membrane inner surface present in at least one body end portion | 300 | 60 | 20 | 300 | 300 | 156 | 200 | 300 | 300 | 22 | 300 | 240 |
| B: Amount (mg/m²) of fat-soluble vitamin per m² of hollow-fiber membrane inner surface present in divided section where vitamin amount is smallest among other divided sections | 230 | 46 | 18 | 30 | 273 | 120 | 20 | 273 | 30 | 20 | 150 | 120 |
| A/B | 1.3 | 1.3 | 1.1 | 10 | 1.1 | 1.3 | 10 | 1.1 | 10 | 1.1 | 2.0 | 2.0 |
| C: Amount (mg/m²) of fat-soluble vitamin per m² of hollow-fiber membrane inner surface present in center portion | 150 | 45 | 20 | 120 | 300 | 120 | 20 | 300 | 300 | 20 | 300 | 120 |
| D: Amount (mg/m²) of fat-soluble vitamin per m² of hollow-fiber membrane inner surface present in outside portion | 230 | 50 | 10 | 30 | 273 | 30 | 15 | 150 | 6 | 15 | 150 | 30 |
| C/D | 0.7 | 0.9 | 2.0 | 4.0 | 1.1 | 4.0 | 1.3 | 2.0 | 50 | 1.3 | 2.0 | 4.0 |
| Antioxidant ability (mg/m²) | ○ 229 | ○ 45 | ○ 17 | ○ 79 | ○ 261 | ○ 119 | ○ 53 | ○ 261 | ○ 79 | ○ 19 | ○ 169 | ○ 135 |
| Standard deviation (variation) of antioxidant ability (mg/m²) | 15 | 15 | 5 | 5 | 5 | 5 | 5 | 5 | 5 | 5 | 5 | 5 |
| E: Water permeation performance (UFR (mL/hr · mmHg)) | 111 | 359 | 434 | 289 | 90 | 223 | 342 | 90 | 289 | 423 | 163 | 201 |
| F: Water permeation performance (UFR (mL/hr · mmHg) of hollow-fiber membrane blood purification device in which fat-soluble vitamin in the same amount as in body end portion is substantially uniformly immobilized in lengthwise direction | 79 | 334 | 424 | 79 | 79 | 188 | 144 | 79 | 79 | 413 | 79 | 113 |
| Increase of water permeation performance (UFR (mL/hr · mmHg)) E-F | ○ 32 | ○ 25 | ○ 10 | ○ 210 | ○ 11 | ○ 35 | ○ 198 | ○ 11 | ○ 210 | ○ 10 | ○ 83 | ○ 88 |
| Lactate dehydrogenase (LDH) activity (Δabs/hr · m²) | ○ 7.7 | ○ 2.3 | ○ 0.9 | ○ 4.1 | ○ 9.1 | ○ 6.7 | ○ 2.7 | ○ 9.1 | ○ 4.1 | ○ 1.0 | ○ 5.7 | ○ 7.5 |

TABLE 2

|   | Example 13 | Example 14 | Example 15 | Example 16 | Example 17 | Example 18 | Example 19 | Comparative Example 1 | Comparative Example 2 | Comparative Example 3 | Comparative Example 4 |
|---|---|---|---|---|---|---|---|---|---|---|---|
| A: Amount (mg/m²) of fat-soluble vitamin per m² of hollow-fiber membrane inner surface present in at least one body end portion | 300 | 77 | 50 | 84 | 36 | 86 | 60 | 340 | 15 | 71 | 84 |

TABLE 2-continued

| | Example 13 | Example 14 | Example 15 | Example 16 | Example 17 | Example 18 | Example 19 | Comparative Example 1 | Comparative Example 2 | Comparative Example 3 | Comparative Example 4 |
|---|---|---|---|---|---|---|---|---|---|---|---|
| B: Amount ($mg/m^2$) of fat-soluble vitamin per $m^2$ of hollow-fiber membrane inner surface present in divided section where vitamin amount is smallest among other divided sections | 30 | 68 | 34 | 58 | 29 | 75 | 46 | 340 | 15 | 71 | 84 |
| A/B | 10 | 1.1 | 1.5 | 1.4 | 1.2 | 1.1 | 1.3 | 1.0 | 1.0 | 1.0 | 1.0 |
| C: Amount ($mg/m^2$) of fat-soluble vitamin per $m^2$ of hollow-fiber membrane inner surface present in center portion | 300 | 68 | 40 | 58 | 29 | 75 | 45 | 340 | 15 | 71 | 84 |
| D: Amount ($mg/m^2$) of fat-soluble vitamin per $m^2$ of hollow-fiber membrane inner surface present in outside portion | 6 | 62 | 50 | 40 | 24 | 68 | 50 | 340 | 15 | 71 | 84 |
| C/D | 50 | 1.1 | 0.8 | 1.5 | 1.2 | 1.1 | 0.9 | 1.0 | 1.0 | 1.0 | 1.0 |
| Antioxidant ability ($mg/m^2$) | ○ 71 | ○ 66 | ○ 35 | ○ 60 | ○ 29 | ○ 73 | ○ 50 | ○ 319 | × 14 | ○ 67 | ○ 79 |
| Standard deviation (variation) of antioxidant ability ($mg/m^2$) | 5 | 5 | 15 | 5 | 5 | 5 | 15 | 20 | 15 | 15 | 20 |
| E: Water permeation performance (UFR (mL/hr · mmHg)) | 289 | 314 | 212 | 327 | 290 | 461 | 351 | 62 | 437 | 313 | 289 |
| F: Water permeation performance (UFR (mL/hr · mmHg) of hollow-fiber membrane blood purification device in which fat-soluble vitamin in the same amount as in body end portion is substantially uniformly immobilized in lengthwise direction | 79 | 302 | 165 | 289 | 83.8 | 86 | 334 | 62 | 437 | 313 | 289 |
| Increase of water permeation performance (UFR (mL/hr · mmHg)) E-F | ○ 210 | ○ 13 | ○ 47 | ○ 38 | ○ 99.5 | ○ 178.5 | ○ 17 | × ○ | × ○ | × ○ | × ○ |
| Lactate dehydrogenase (LDH) activity (Δabs/hr · $m^2$) | ○ 4.1 | ○ 3.4 | ○ 11.7 | ○ 3.1 | ○ 5.1 | ○ 22.2 | ○ 2.5 | × 270 | ○ 0.7 | ○ 3.4 | ○ 4.1 |

This application is based upon the prior Japanese patent application (Japanese Patent Application No. 2013-259551) filed on Dec. 16, 2013, the entire contents of which are incorporated herein by reference.

INDUSTRIAL APPLICABILITY

The present invention can provide a hollow-fiber membrane blood purification device that reduces complications and is excellent in biocompatibility. The hollow-fiber membrane blood purification device of the present invention has industrial applicability in a blood purification therapy.

REFERENCE SIGNS LIST 1 hollow-fiber membrane
1a first passage
2 cylindrical vessel
2a, 2b port
3a, 3b sealing resin
6a, 6b nozzle
7a, 7b header cap
8 header internal space
10 hollow-fiber membrane blood purification device
11 second passage
Fa flowing direction of treatment liquid 1 (such as dialysate or blood)
Fb flowing direction of treatment liquid 2 (such as blood)

The invention claimed is:

1. A hollow-fiber membrane blood purification device comprising hollow-fiber membranes filled in a vessel,
wherein the hollow-fiber membranes contain a hydrophobic polymer, a hydrophilic polymer and a fat-soluble vitamin,
when a hollow-fiber membrane bundle is divided into five equally sized sections in a lengthwise direction and divided sections positioned in endmost portions are defined as body end portions, an amount of the fat-soluble vitamin present in at least one of the body end portions is the largest amount of the fat-soluble vitamin present in any of the individual divided sections, and an amount of the fat-soluble vitamin per $m^2$ of a hollow-fiber membrane inner surface of the at least one body end portion is 20 $mg/m^2$ or more and 300 $mg/m^2$ or less.

2. The hollow-fiber membrane blood purification device according to claim 1, wherein when an amount of the fat-soluble vitamin per $m^2$ of the hollow-fiber membrane inner surface present in the body end portion where the amount of the fat-soluble vitamin is the largest is defined as A ($mg/m^2$) and an amount of the fat-soluble vitamin per $m^2$ of the hollow-fiber membrane inner surface present in a divided section where the amount of the fat-soluble vitamin is the smallest among the other divided sections is defined as B (mg/m2), a ratio (A/B) between the amounts A and B is 1.1 or more and 10 or less.

3. The hollow-fiber membrane blood purification device according to claim 2, wherein the ratio (A/B) between the amounts A and B is 1.3 or more and 10 or less.

4. The hollow-fiber membrane blood purification device according to claim 3, wherein when within an inner circle having a ½ radius of the hollow-fiber membrane bundle is defined as a center portion and a portion not included in the center portion is defined as an outside portion, an amount of the fat-soluble vitamin per m² of the hollow-fiber membrane inner surface present in the center portion is larger than an amount of the fat-soluble vitamin per m² of the hollow-fiber membrane inner surface present in the outside portion.

5. The hollow-fiber membrane blood purification device according to claim 4, wherein when the amount of the fat-soluble vitamin per m² of the hollow-fiber membrane inner surface present in the center portion is defined as C (mg/m²) and the amount of the fat-soluble vitamin per m² of the hollow-fiber membrane inner surface present in the outside portion is defined as D (mg/m²), a ratio (C/D) between the amounts C and D is 1.1 or more and 50 or less.

6. The hollow-fiber membrane blood purification device according to claim 5, wherein the hydrophilic polymer is polyvinylpyrrolidone.

7. The hollow-fiber membrane blood purification device according to claim 2, wherein when within an inner circle having a ½ radius of the hollow-fiber membrane bundle is defined as a center portion and a portion not included in the center portion is defined as an outside portion, an amount of the fat-soluble vitamin per m² of the hollow-fiber membrane inner surface present in the center portion is larger than an amount of the fat-soluble vitamin per m² of the hollow-fiber membrane inner surface present in the outside portion.

8. The hollow-fiber membrane blood purification device according to claim 7, wherein when the amount of the fat-soluble vitamin per m² of the hollow-fiber membrane inner surface present in the center portion is defined as C (mg/m²) and the amount of the fat-soluble vitamin per m² of the hollow-fiber membrane inner surface present in the outside portion is defined as D (mg/m²), a ratio (C/D) between the amounts C and D is 1.1 or more and 50 or less.

9. The hollow-fiber membrane blood purification device according to claim 8, wherein the hydrophilic polymer is polyvinylpyrrolidone.

10. The hollow-fiber membrane blood purification device according to claim 1, wherein when within an inner circle having a ½ radius of the hollow-fiber membrane bundle is defined as a center portion and a portion not included in the center portion is defined as an outside portion, an amount of the fat-soluble vitamin per m² of the hollow-fiber membrane inner surface present in the center portion is larger than an amount of the fat-soluble vitamin per m² of the hollow-fiber membrane inner surface present in the outside portion.

11. The hollow-fiber membrane blood purification device according to claim 10, wherein when the amount of the fat-soluble vitamin per m² of the hollow-fiber membrane inner surface present in the center portion is defined as C (mg/m²) and the amount of the fat-soluble vitamin per m² of the hollow-fiber membrane inner surface present in the outside portion is defined as D (mg/m²), a ratio (C/D) between the amounts C and D is 1.1 or more and 50 or less.

12. The hollow-fiber membrane blood purification device according to claim 11, wherein the hydrophilic polymer is polyvinylpyrrolidone.

13. The hollow-fiber membrane blood purification device according to claim 1, wherein the hydrophobic polymer has a solubility parameter δ (cal/cm³)$^{1/2}$ of 13.0 or less.

14. The hollow-fiber membrane blood purification device according to claim 13, wherein the hydrophilic polymer is polyvinylpyrrolidone.

15. The hollow-fiber membrane blood purification device according to claim 1, wherein the hydrophobic polymer is any one selected from the group consisting of polysulfones, polyethersulfones and cellulose acetates.

16. The hollow-fiber membrane blood purification device according to claim 15, wherein the hydrophilic polymer is polyvinylpyrrolidone.

17. The hollow-fiber membrane blood purification device according to claim 1, wherein the hydrophilic polymer is polyvinylpyrrolidone.

* * * * *